United States Patent
Corbin et al.

(10) Patent No.: US 11,126,627 B2
(45) Date of Patent: Sep. 21, 2021

(54) SYSTEM AND METHOD FOR DYNAMIC TRANSACTIONAL DATA STREAMING

(71) Applicant: Change Healthcare Holdings, LLC, Nashville, TN (US)

(72) Inventors: Brian Scott Corbin, San Mateo, CA (US); Thomas Dixon Whitmire, IV, San Mateo, CA (US); Theodore Calhoun Tanner, Jr., San Mateo, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 339 days.

(21) Appl. No.: 14/466,907

(22) Filed: Aug. 22, 2014

(65) Prior Publication Data

US 2015/0199482 A1 Jul. 16, 2015

Related U.S. Application Data

(60) Provisional application No. 61/927,261, filed on Jan. 14, 2014.

(51) Int. Cl.
  *G06F 16/2455* (2019.01)
  *G16H 40/67* (2018.01)
  *G06Q 10/10* (2012.01)

(52) U.S. Cl.
  CPC ....... *G06F 16/24568* (2019.01); *G06Q 10/10* (2013.01); *G16H 40/67* (2018.01)

(58) Field of Classification Search
  CPC ............ G06F 17/30516; G06F 19/328; G06F 16/24568; G06F 19/3418; G06F 16/254; G06Q 50/22; G06Q 50/24; G06Q 10/00; G06Q 10/10; G16H 10/60; G16H 15/00; G16H 40/67

USPC .......................................................... 705/2
See application file for complete search history.

(56) References Cited

U.S. PATENT DOCUMENTS

| | | | |
|---|---|---|---|
| 5,872,021 A | 2/1999 | Matsumoto et al. | |
| 6,477,580 B1 * | 11/2002 | Bowman-Amuah | G06F 9/54 709/231 |
| 6,546,428 B2 * | 4/2003 | Baber | H04L 47/10 709/230 |
| 7,386,565 B1 | 6/2008 | Singh et al. | |
| 7,917,378 B2 | 3/2011 | Fitzgerald et al. | |
| 7,917,515 B1 * | 3/2011 | Lemoine | G06F 17/2247 707/741 |
| 7,970,802 B2 * | 6/2011 | Ishizaki | G06F 17/30938 707/796 |

(Continued)

FOREIGN PATENT DOCUMENTS

| | | | |
|---|---|---|---|
| GB | 2478440 | 10/2013 | |
| WO | WO20071435599 A2 * | 12/2007 | G06Q 10/10 |

(Continued)

OTHER PUBLICATIONS

Version 5010 and D.0, Center for Medicare & Medicaid Services, p. 1.*

(Continued)

*Primary Examiner* — Elaine Gort
*Assistant Examiner* — Teresa S Williams
(74) *Attorney, Agent, or Firm* — Meunier Carlin & Curfman LLC

(57) ABSTRACT

A system and method for dynamic transactional data streaming are provided.

20 Claims, 15 Drawing Sheets

(56) References Cited

U.S. PATENT DOCUMENTS

| Patent/Publication No. | Date | Inventor(s) |
|---|---|---|
| 7,992,153 B2 | 8/2011 | Ban |
| 8,060,395 B1 | 11/2011 | Frasher et al. |
| 8,073,801 B1 | 12/2011 | Von Halle et al. |
| 8,095,975 B2 | 1/2012 | Boss et al. |
| 8,103,667 B2 | 1/2012 | Azar et al. |
| 8,103,952 B2 * | 1/2012 | Hopp ............... G06F 17/2247 715/234 |
| 8,203,562 B1 | 6/2012 | Alben et al. |
| 8,229,808 B1 | 7/2012 | Heit |
| 8,286,191 B2 | 10/2012 | Amini et al. |
| 8,359,298 B2 | 1/2013 | Schacher et al. |
| 8,364,501 B2 | 1/2013 | Rana et al. |
| 8,417,755 B1 | 4/2013 | Zimmer |
| 8,495,108 B2 | 7/2013 | Nagpal et al. |
| 8,515,777 B1 | 8/2013 | Rajasenan |
| 8,527,522 B2 | 9/2013 | Baron |
| 8,817,665 B2 | 8/2014 | Thubert et al. |
| 8,984,464 B1 | 3/2015 | Mihal et al. |
| 9,165,045 B2 | 10/2015 | Mok et al. |
| 9,208,284 B1 | 12/2015 | Douglass |
| 2002/0022973 A1 | 2/2002 | Sun et al. |
| 2002/0038233 A1 | 3/2002 | Shubov et al. |
| 2002/0165738 A1 | 11/2002 | Dang |
| 2003/0055668 A1 | 3/2003 | Saran et al. |
| 2003/0097359 A1 | 5/2003 | Ruediger |
| 2003/0171953 A1 | 9/2003 | Narayanan et al. |
| 2003/0217159 A1 | 11/2003 | Schramm-Apple et al. |
| 2003/0233252 A1 * | 12/2003 | Haskell ............... G06F 19/322 705/2 |
| 2004/0143446 A1 | 7/2004 | Lawrence |
| 2005/0010452 A1 * | 1/2005 | Lusen ............... G06Q 10/10 705/3 |
| 2005/0071189 A1 | 3/2005 | Blake et al. |
| 2005/0102170 A1 * | 5/2005 | Lefever ............... G06Q 40/08 705/4 |
| 2005/0137912 A1 | 6/2005 | Rao et al. |
| 2005/0152520 A1 | 7/2005 | Logue |
| 2005/0182780 A1 | 8/2005 | Forman et al. |
| 2005/0222912 A1 | 10/2005 | Chambers |
| 2006/0036478 A1 | 2/2006 | Aleynikov et al. |
| 2006/0074290 A1 | 4/2006 | Chen et al. |
| 2006/0089862 A1 | 4/2006 | Anandarao et al. |
| 2006/0129428 A1 | 6/2006 | Wennberg |
| 2006/0136264 A1 | 6/2006 | Eaton et al. |
| 2006/0206358 A1 * | 9/2006 | Beaver ............... G06Q 10/10 705/2 |
| 2007/0113172 A1 * | 5/2007 | Behrens ............... G06F 17/2229 715/239 |
| 2007/0118399 A1 | 5/2007 | Avinash et al. |
| 2007/0156455 A1 | 7/2007 | Tarino et al. |
| 2007/0174101 A1 | 7/2007 | Li et al. |
| 2007/0180451 A1 | 8/2007 | Ryan et al. |
| 2007/0214133 A1 | 9/2007 | Liberty et al. |
| 2007/0233603 A1 | 10/2007 | Schmidgall et al. |
| 2007/0260492 A1 | 11/2007 | Feied et al. |
| 2007/0276858 A1 | 11/2007 | Cushman et al. |
| 2007/0288262 A1 | 12/2007 | Sakaue et al. |
| 2008/0013808 A1 | 1/2008 | Russo et al. |
| 2008/0046292 A1 | 2/2008 | Mayers |
| 2008/0082980 A1 | 4/2008 | Nessland et al. |
| 2008/0091592 A1 | 4/2008 | Blackburn et al. |
| 2008/0126264 A1 | 5/2008 | Tellefsen et al. |
| 2008/0133436 A1 | 6/2008 | Di Profio |
| 2008/0215993 A1 | 9/2008 | Rossman |
| 2008/0288292 A1 | 11/2008 | Bi et al. |
| 2008/0295094 A1 | 11/2008 | Korupolu et al. |
| 2008/0319983 A1 | 12/2008 | Meadows |
| 2009/0083664 A1 | 3/2009 | Bay |
| 2009/0125796 A1 | 5/2009 | Day et al. |
| 2009/0192864 A1 | 7/2009 | Song et al. |
| 2009/0198520 A1 | 8/2009 | Piovanetti-Perez |
| 2009/0300054 A1 * | 12/2009 | Fisher ............... G06F 17/30569 |
| 2009/0307104 A1 | 12/2009 | Weng |
| 2009/0313045 A1 | 12/2009 | Boyce |
| 2010/0017222 A1 | 1/2010 | Yeluri |
| 2010/0070303 A1 | 3/2010 | Massoumi |
| 2010/0076950 A1 | 3/2010 | Kenedy et al. |
| 2010/0082620 A1 | 4/2010 | Jennings, III et al. |
| 2010/0088108 A1 | 4/2010 | Machado |
| 2010/0088119 A1 | 4/2010 | Tipirneni |
| 2010/0138243 A1 | 6/2010 | Carroll |
| 2010/0217973 A1 | 8/2010 | Kress et al. |
| 2010/0228565 A1 | 9/2010 | Kharraz Tavakol |
| 2010/0228721 A1 | 9/2010 | Mok et al. |
| 2010/0295674 A1 | 11/2010 | Hsieh et al. |
| 2010/0332273 A1 | 12/2010 | Balasubramanian et al. |
| 2011/0009707 A1 | 1/2011 | Kaundinya |
| 2011/0015947 A1 | 1/2011 | Erry et al. |
| 2011/0055252 A1 | 3/2011 | Kapochunas et al. |
| 2011/0071857 A1 | 3/2011 | Malov et al. |
| 2011/0137672 A1 | 6/2011 | Adams et al. |
| 2011/0218827 A1 | 9/2011 | Kennefick et al. |
| 2012/0004943 A1 | 1/2012 | Reichman |
| 2012/0011029 A1 | 1/2012 | Thomas et al. |
| 2012/0035984 A1 | 2/2012 | Srinivasa et al. |
| 2012/0078940 A1 | 3/2012 | Kolluri et al. |
| 2012/0130736 A1 | 5/2012 | Dunston et al. |
| 2012/0158429 A1 | 6/2012 | Murawski et al. |
| 2012/0158750 A1 | 6/2012 | Faulkner et al. |
| 2012/0173279 A1 | 7/2012 | Nessa et al. |
| 2012/0245958 A1 | 9/2012 | Lawrence et al. |
| 2012/0246727 A1 | 9/2012 | Elovici et al. |
| 2012/0290320 A1 | 11/2012 | Kurgan et al. |
| 2012/0290564 A1 | 11/2012 | Mok et al. |
| 2013/0030827 A1 | 1/2013 | Snyder et al. |
| 2013/0044749 A1 | 2/2013 | Eisner et al. |
| 2013/0085769 A1 | 4/2013 | Jost et al. |
| 2013/0138554 A1 | 5/2013 | Nikankin et al. |
| 2013/0166552 A1 | 6/2013 | Rozenwald et al. |
| 2013/0204940 A1 | 8/2013 | Kinsel et al. |
| 2013/0290007 A1 | 10/2013 | Haq |
| 2013/0304903 A1 | 11/2013 | Mick et al. |
| 2014/0046931 A1 | 2/2014 | Mok et al. |
| 2014/0056243 A1 | 2/2014 | Pelletier et al. |
| 2014/0059084 A1 | 2/2014 | Adams et al. |
| 2014/0088981 A1 | 3/2014 | Momita |
| 2014/0136233 A1 | 5/2014 | Atkinson et al. |
| 2014/0207509 A1 | 7/2014 | Yu |
| 2014/0222482 A1 | 8/2014 | Gautam et al. |
| 2014/0244300 A1 | 8/2014 | Bess et al. |
| 2014/0249878 A1 | 9/2014 | Kaufman et al. |
| 2014/0278491 A1 | 9/2014 | Weiss |
| 2014/0358578 A1 | 12/2014 | Ptachcinski |
| 2014/0358845 A1 | 12/2014 | Mundlapudi et al. |
| 2015/0095056 A1 | 4/2015 | Ryan et al. |
| 2015/0112696 A1 | 4/2015 | Kharraz Tavakol |
| 2015/0142464 A1 | 5/2015 | Rusin et al. |
| 2015/0142495 A1 | 5/2015 | Garakani |
| 2015/0154528 A1 | 6/2015 | Kharraz Tavakol |
| 2015/0199482 A1 | 7/2015 | Corbin et al. |
| 2015/0332283 A1 | 11/2015 | Witchey |
| 2016/0028552 A1 | 1/2016 | Spanos et al. |
| 2016/0055205 A1 | 2/2016 | Jonathan et al. |
| 2016/0253679 A1 | 9/2016 | Venkatraman et al. |
| 2016/0328641 A1 | 11/2016 | Alsaud et al. |
| 2016/0342750 A1 | 11/2016 | Alstad et al. |
| 2016/0342751 A1 | 11/2016 | Alstad et al. |
| 2017/0060856 A1 | 3/2017 | Turtle |
| 2017/0091397 A1 | 3/2017 | Shah et al. |
| 2017/0103164 A1 | 4/2017 | Dunlevy et al. |
| 2017/0103165 A1 | 4/2017 | Dunlevy et al. |
| 2017/0132621 A1 | 5/2017 | Miller et al. |
| 2017/0351821 A1 | 12/2017 | Tanner et al. |

(56) References Cited

U.S. PATENT DOCUMENTS

2017/0372300 A1    12/2017   Dunlevy et al.
2020/0073729 A1*   3/2020   Sturtivant ........... G06F 9/44526

FOREIGN PATENT DOCUMENTS

WO     WO 2012/122065     9/2012
WO     WO2012/122065     9/2012

OTHER PUBLICATIONS

Ira J. Kalet, Robert S. Giansiracusa, Jonathan Jacky, Dora Avitan, A declarative implementation of the DICOM-3 network protocol, ELSEVIER, Biomedical Informatics, vol. 36, Issue 3, Jun. 2003, pp. 159-176 (Year: 2003).*

PCT International Search Report of PCT/US14/52764; dated Nov. 21, 2014; (2 pgs.).

PCT Written Opinion of the International Searching Authority of PCT/US14/52764; dated Nov. 21, 2014; (5 pgs.).

"New Health Care Electronic Transactions Standards Versions 5010, D.0, and 3.0"; Jan. 2010 ICN 903192; http://www.cms.gov/Regulations-and-Guidance/HIPAA-Adminstrative-Simplification/Versions501andD0/downloads.w5010BasicsFctCht.pdf; (4 pgs.).

Ahlswede et al., *Network Information Flow*, IEEE Transactions on Information Theory, vol. 46, No. 4; Jul. 2000 (13 pgs.).

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

Domingos et al., *Mining High-Speed Data Streams*, (2000) (10 pgs.).

Greenhalgh et al., *Diffusion of Innovations in Health Service Organisations—a systematic literature review*, Blackwell Publishing, 2005 (325 pgs.).

Jackson et al., *The Evolution of Social and Economic Networks*, Journal of Economic Theory 106, pp. 265-295, 2002 (31 pgs.).

Jackson, Matthew O., *Social and Economic Networks*, Princeton University Press, 2008 (509 pgs.).

Krempl et al., *Open Challenges for Data Stream Mining Research*, SIGKDD Explorations, vol. 16, Issue 1, Jun. 2014 (64 pgs.).

Rebuge, *Business Process Analysis in Healthcare Environments*, 2011, Ellsevier Ltd., pp. 99-116 (18 pgs.).

Wasserman et al., *Social Network Analysis: Methods and Applications*, Cambridge University Press; 1994 (434 pgs.).

White et al., *Algorithms for Estimating Relative Importance in Networks*, Proceedings of the Ninth ACM SIGKDD International Conference on Knowledge Discovery and Data Mining, 2003 (10 pgs.).

(MATHJAX), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).

Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).

Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).

Lin et al., A simplicial complex, a hypergraph, structure in the latent semantic space of document clustering, © 2005 Elsevier Inc. (26 pgs.).

Anonymous: "Oauth—Wikipedia", Sep. 23, 2013. Retrieved from the Internet URL:https://en.wikipedia.org/w/index.php?title+oAuth&oldid+574187532 (3 pages).

Anonymous: "Oauth" Wikipedia—Retrieved from the Internet URL:https://en.wikipedia.org/wiki/Oauth (8 pgs.)

* cited by examiner

```
ISA*00*     *00*     *ZZ* 1234567890    *ZZ* 654456654
*130810*0409*^*00501*100000001*0*P*:~
GS*HS* 1234567890* 654456654*20130810*0409*1*X*005010X279A1~
ST*270*0001*005010X279A1~
BHT*0022*13*137083739083716126837*20130810*0409~
HL*1**20*1~
NM1*PR*2*MOCK PAYER FOR TESTING*****PI*MOCKPAYER~
HL*2*1*21*1~
NM1*1P*1*LEE*GARY****XX*1497834352~
HL*3*2*22*0~
TRN*1*1*1453915417~
NM1*IL*1*BUSHHOG*BILLYBOB****MI*W199138913~
DMG*D8*19770101~
DTP*291*D8*20130810~
EQ*30~
SE*13*0001~
GE*1*1~
GS*BE*1234567890*654456654*20130809*1150*2*X*005010X220A1~
ST*834*0002*005010X220A1~
BGN*00*12456*20130809*1150*ET***2~
N1*P5*KOELPIN AND SONS*FI*999888777~
N1*IN*REICHERT-SCHROEDER*FI*654456654~
INS*Y*18*021*20*A***FT~
REF*0F*123456789~
REF*1L*123456001~
DTP*356*D8*20130809~
NM1*IL*1*BROWN*ADELIA****34*123456789~
PER*IP**HP*951-768-7732 x17235*WP*728.783.0678 x2392**~
N3*9702 NICOLE MEADOWS*SUITE 370~
N4*EAST WYMANMOUTH*LA*67175****~
DMG*D8*19870914*F~
HD*021**HLT~
DTP*348*D8*20130809~
COB*P*890111*5~
HD*021**DEN~
DTP*348*D8*20130809~
HD*021**VIS~
DTP*348*D8*20130809~
SE*21*0002~
GE*1**2~
IEA*1*100000001~
```

FIGURE 13

SYSTEM AND METHOD FOR DYNAMIC TRANSACTIONAL DATA STREAMING

PRIORITY CLAIMS/RELATED APPLICATIONS

This application claims the benefit and priority under 35 USC 119(e) to U.S. Provisional Patent Application Ser. No. 61/927,261, filed on Jan. 14, 2014 and entitled "System and Method for Dynamic Transactional Data Streaming", the entirety of which is incorporated herein by reference.

FIELD

The disclosure relates generally to a transactional data streaming system and in particular to a data streaming system that may be used for health care related data.

BACKGROUND

With the desire to lower health care costs, the United States has implemented a new health care system that, among other things, fosters competition among health care providers using healthcare marketplaces. However, the true costs of health care lie hidden in the inefficient access, delivery and payment systems that have escaped innovation and disruption until now. More specifically, the transmission and reception of health care information within the context of care for the consumer has languished in past orthodoxies of obfuscated technologies and data standards. Thus, the data pipelines for fluid enablement of base costs for health care have been the main impediment to accessible transparent costs within the Health Industry. The current industry standard for electronic transmission of health are data is called HIPPA ASC X12 5010 per the Health Insurance Portability & Accountability Act (HIPPA) of 1996.

HIPAA was supposed to make the health care system in the United States more efficient by standardizing health care transactions. To with the acronym says Portability not Privacy. HIPAA added a new Part C titled "Administrative Simplification" to Title XI of the Social Security Act. This effort was created to supposedly simplify health care transactions by requiring all health plans to engage in health care transactions in a standardized way.

However, HIPAA has actually created a market for IT companies that have in fact inflated the true cost of care services. More specifically, there are several companies that charge for basic Application Programming Interfaces (API), Claims eligibility and enrollment processing under HIPAA. Furthermore, there are several clearinghouses that charge for basic Electronic Data Interchange (EDI).

Thus, many companies that support HIPPA ASC x12 5010 standards inject huge hidden costs within the Health IT processing flows. This is both an infrastructure cost and a usage charge. It is desirable for these costs to be as close to zero as possible in order for the consumer to truly know the cost of care for a service that is based on the current day and date.

The majority of existing Health IT systems are legacy data systems, conveying transactional information by means of sub-optimal file formats. The transactional data contained in these files can be difficult to generate and parse. Some systems are unable to work with these files unless they can be completely loaded into memory at once.

BRIEF DESCRIPTION OF THE DRAWINGS

FIG. 13 illustrates a ASCX12 5010 sample input file, containing both eligibility (270) and enrollment (834) transactions.

DETAILED DESCRIPTION OF ONE OR MORE EMBODIMENTS

The disclosure is particularly applicable to a healthcare marketplace system that uses the dynamic transactional data streaming and it is in this context that the disclosure will be described. It will be appreciated, however, that the dynamic transactional data streaming has greater utility since it may be implemented in different ways than those described below and may be used without the healthcare marketplace system or used with other systems that can take advantage of the benefits of the dynamic transactional data streaming.

The HIPPA ASC X12 5010 standard defines a number of different health care related transactions and code sets including:

(270/271) for health care eligibility inquiry and response transactions
(274) for health care provider information
(275) for patient information
(276/277) for health care claims, status, and acknowledgement transactions
(278) for health care services review
(834/835/837) for Benefit Enrollment, Claim Payment and Care Claim transactions.

Although the disclosure below is directed to an example of the system that uses HIPPA ASC X12 5010 standard, the transactional data streaming system and method may be used with various standards or later revisions of the X12 standard since the system and method could be easily adjusted to work with the various standards or later revisions of the X12 standard.

As described above, the current systems inject huge health care IT costs into the process and thus the system and method provide a low cost pipeline that would enable the above transactions. The system and method may also provide a topology that enables lower costs along with a "graph based" representation of several data sources that includes the entire HIPPA ASC X12 5010 standard.

The system and method provide a technique to efficiently process this health care related information as dynamic transactional data streams. In one aspect of the system, each file may be processed using streaming to minimize the memory footprint. As the transactional data moves through the system, the transactional data may be dynamically analyzed so that rules for parsing and processing the data can be loaded up at run time. As the context changes in the data stream, new rules can be injected to adjust the data processing. Dynamic rule injection also provides for minimized system downtime as new behaviors can be added while data is streaming through the system.

Figure 1A:
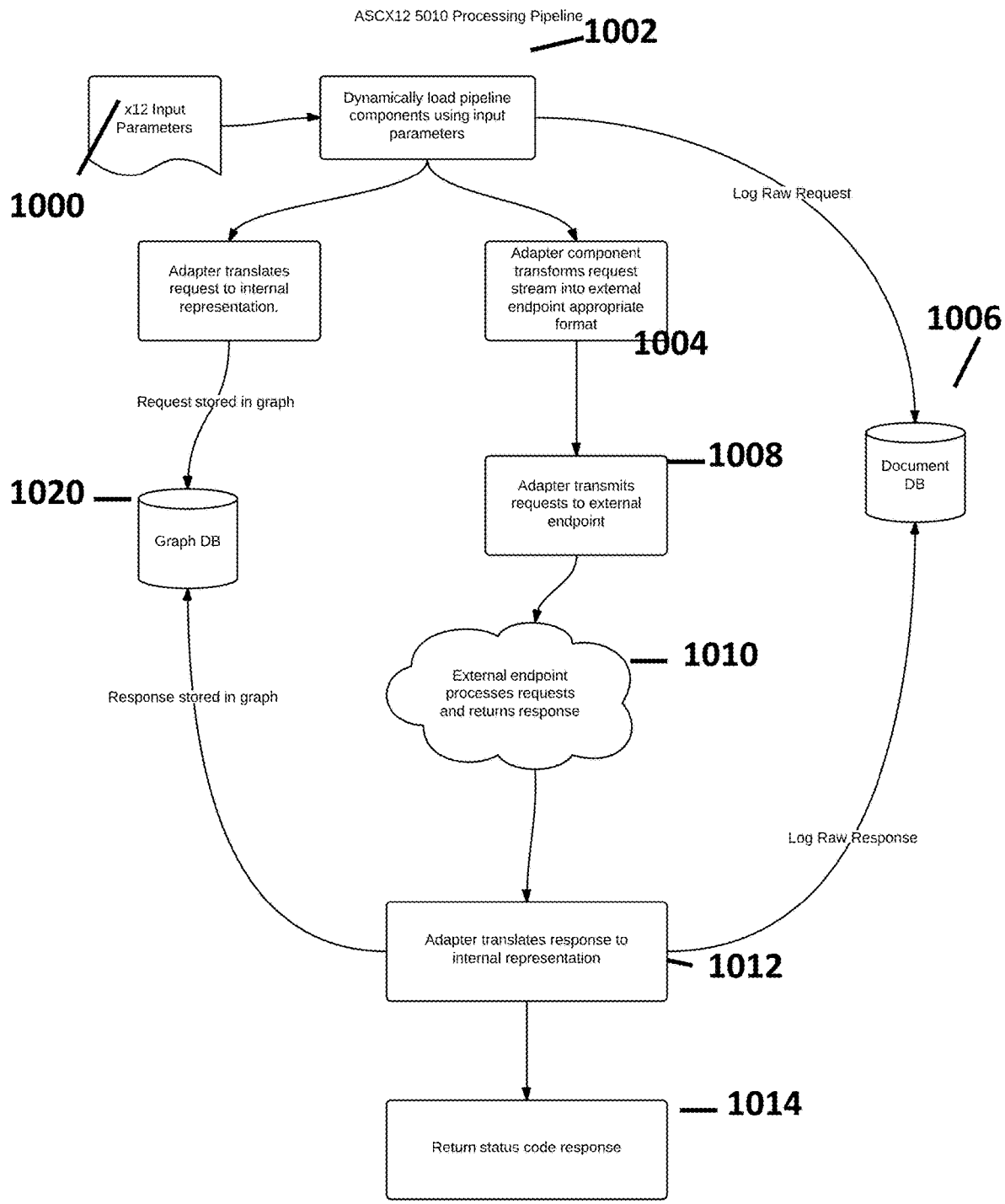
FIG. 1A illustrates an example of an ASCX12 5010 Processing Pipeline.

To understand the dynamic transactional data streaming system and method, first an example of the processing pipeline for the ASC X12 5010 standard is described with reference to FIG. 1A. As shown in FIG. 1A, the processing pipeline may receive one or more ×12 input parameters (1000) that may be dynamically loaded into pipeline components (1002.) The system logs the raw request in a document database, prior to executing the adapter. The system may use an adapter component 1004 to transform the request stream to separate internal and external endpoint data formats as described below with reference to FIGS. 1B and 2-4. Examples of data formats include, but are not limited to XML, SOAP messages, JSON, delimited data formats, etc. The system's internal data format is used throughout the system to ensure that data is processed in a uniform manner. External endpoint data formats vary based on the requirements of the external endpoint, and are generated based on the adapter component's configuration. The adapter component 1004 transmits the transformed request stream to the external endpoint. The external endpoint then processes the request, and returns a response. The system logs the response stream into a document database. The adapter component may then translate the response to the internal representation, which is then persisted in the graph database. Then, the status code response is returned to the original requestor to complete the processing pipeline.

Figure 1B:
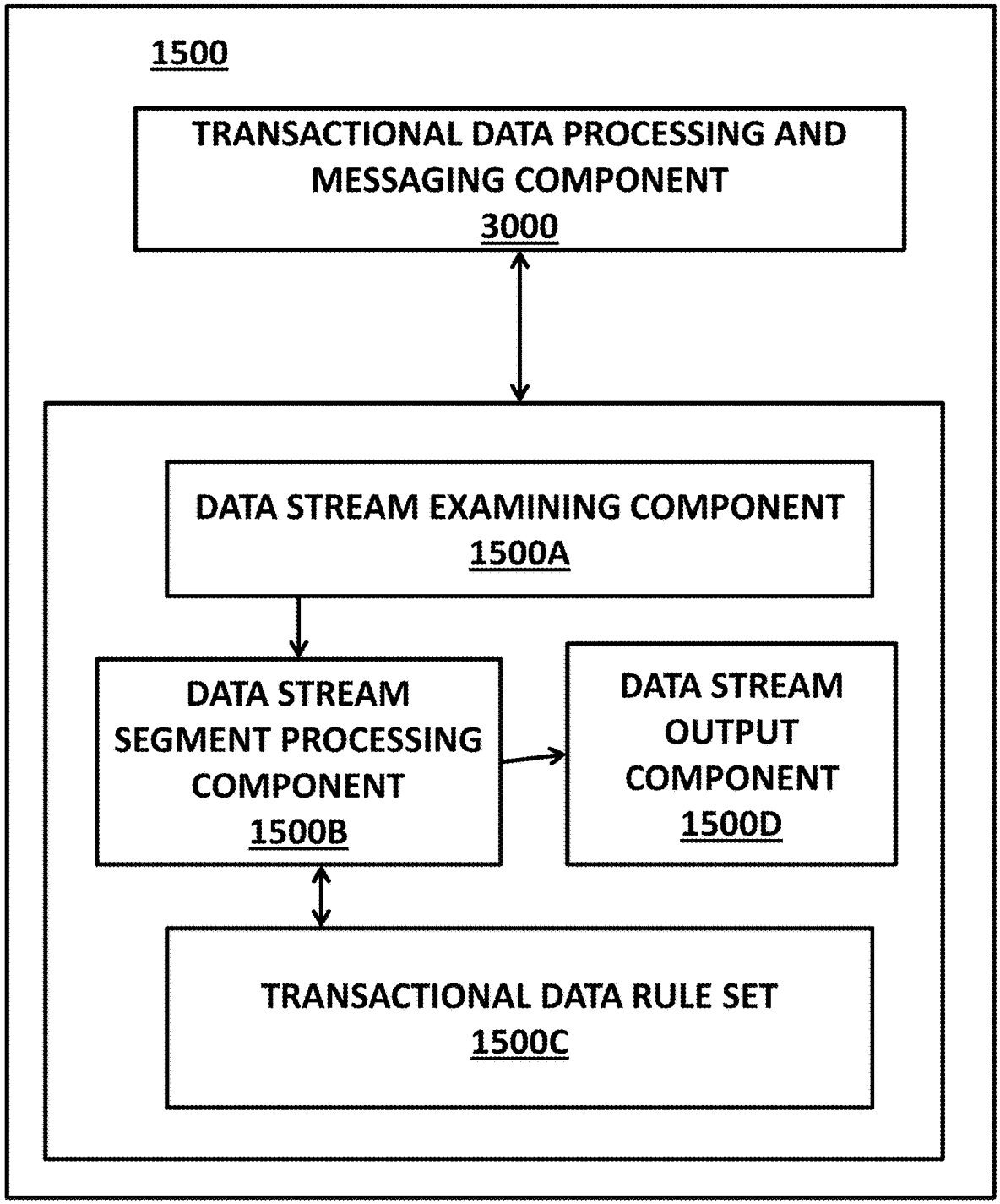
FIG. 1B illustrates an implementation of a dynamic transactional data stream introspection and processing system that may be implemented in the adapter.

FIG. 1B illustrates an implementation of a dynamic transactional data stream introspection and processing system 1500 that may be implemented, for example in the adapter 1004 shown in FIG. 1A. The system 1500 may have a processing and messaging component 3000 that is described in more detail with reference to FIG. 3 that may be used to facilitate the functions of the components 1500A, 1500B, 1500C and 1500D of the system. The system 1500 and each component of the system may be implemented in a combination of hardware and software using one or more computing resources, such as one or more server computers or one or more cloud computing resources that have one or more processors and a memory connected to the one or more processors. In this implementation, each of the components of the system may be a plurality of lines of code that may be executed by the processor of the computing resources. Alternatively, each of the components of the system may be a hardware device (or all of the components implemented in one hardware device) wherein the hardware device, based on logic programmed to implement the functions and operations of the components described below, may implement each component. The hardware device may be a microcontroller, a processor, a programmable logic device, a field programmable gate array, an application specific integrated circuit and the like. For example, each component may be implemented by a hardware processor that is configured to perform the operations and functions of the component.

Figure 2:
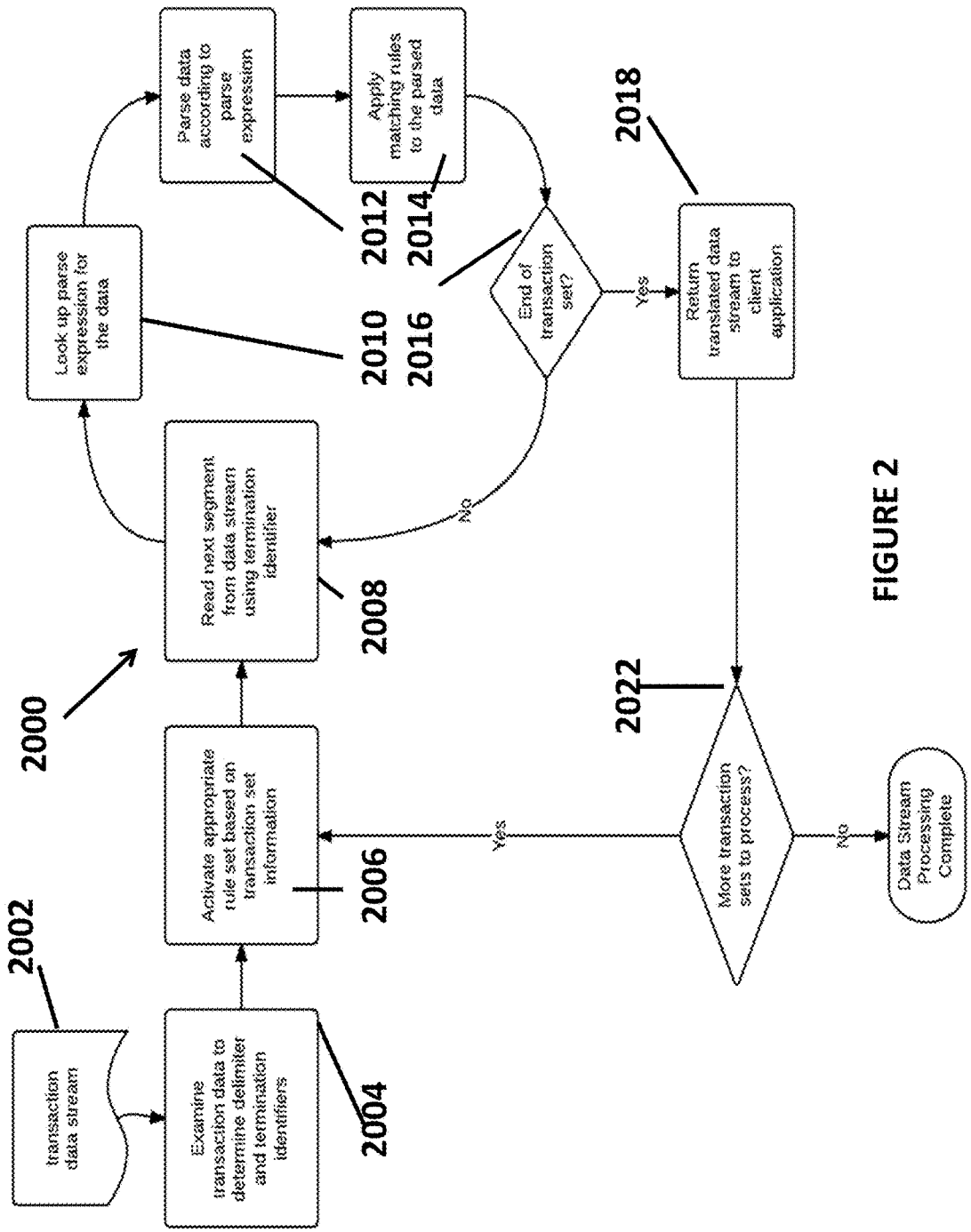
FIG. 2 illustrates a dynamic transactional data stream introspection and processing method that may be implemented, for example, by the system implementation in FIG. 1B.

Returning to FIG. 1B, the system 1500 may further have a data stream examining component 1500A that performs initial analysis of the transactional data stream as described in more detail in process 2004 in FIG. 2. The system 1500 may further have a data stream segment processing component 1500B that analyzes and processes each segment of each data stream and selects an appropriate rule set to use for the processing based on the information/data in the particular transaction datastream being currently processed as described in more detail in processes 2006-2022 in FIG. 2. The system 1500 may further have a transactional data rule set store 1500C that stores a plurality of rule sets that may be selected by the data stream segment processing component 1500B. Thus, using the rule set store 1500C and the data stream segment processing component 1500B, as the transactional data moves through the system, the transactional data may be dynamically analyzed so that rules for parsing and processing the data (the rule sets in the rule set store 1500C) can be loaded up at run time. Furthermore, as the context changes in the data stream, new rules can be injected into the rule set store 1500C or selected by the data stream segment processing component 1500B from the already existing rule sets in the rule set store 1500C to adjust the data processing. Dynamic rule injection also provides for minimized system downtime as new behaviors can be added while data is streaming through the system.

To illustrate how rule sets are dynamically applied to transaction sets, consider a ASCX12 5010 file containing both eligibility and enrollment transaction sets as shown in FIG. 13. In the ASC X12 5010 file specification, functional groups are used to group transactions by transaction types. Transaction data is contained within a functional group within a transaction set. The functional group acts as an outer envelope for one or more transaction sets, and is delimited using GS and GE segments. ST and SE segments enclose data within a transaction set. The system parses the GS and ST segments and infers which rule sets are used, based on the transaction type as follows in this example:

| ASCX12 5010 Control Segments | Transaction Set Identifiers |
|---|---|
| GS*HS* 1234567890* 654456654*20130810*0409*1*X*005010X279A1~ | 005010X279A1 (Transaction Version) |
| ST*270*0001*005010X279A1 | 270 (Transaction Set Type) 005010X279A1 (Transaction Version) |

Figure 3:
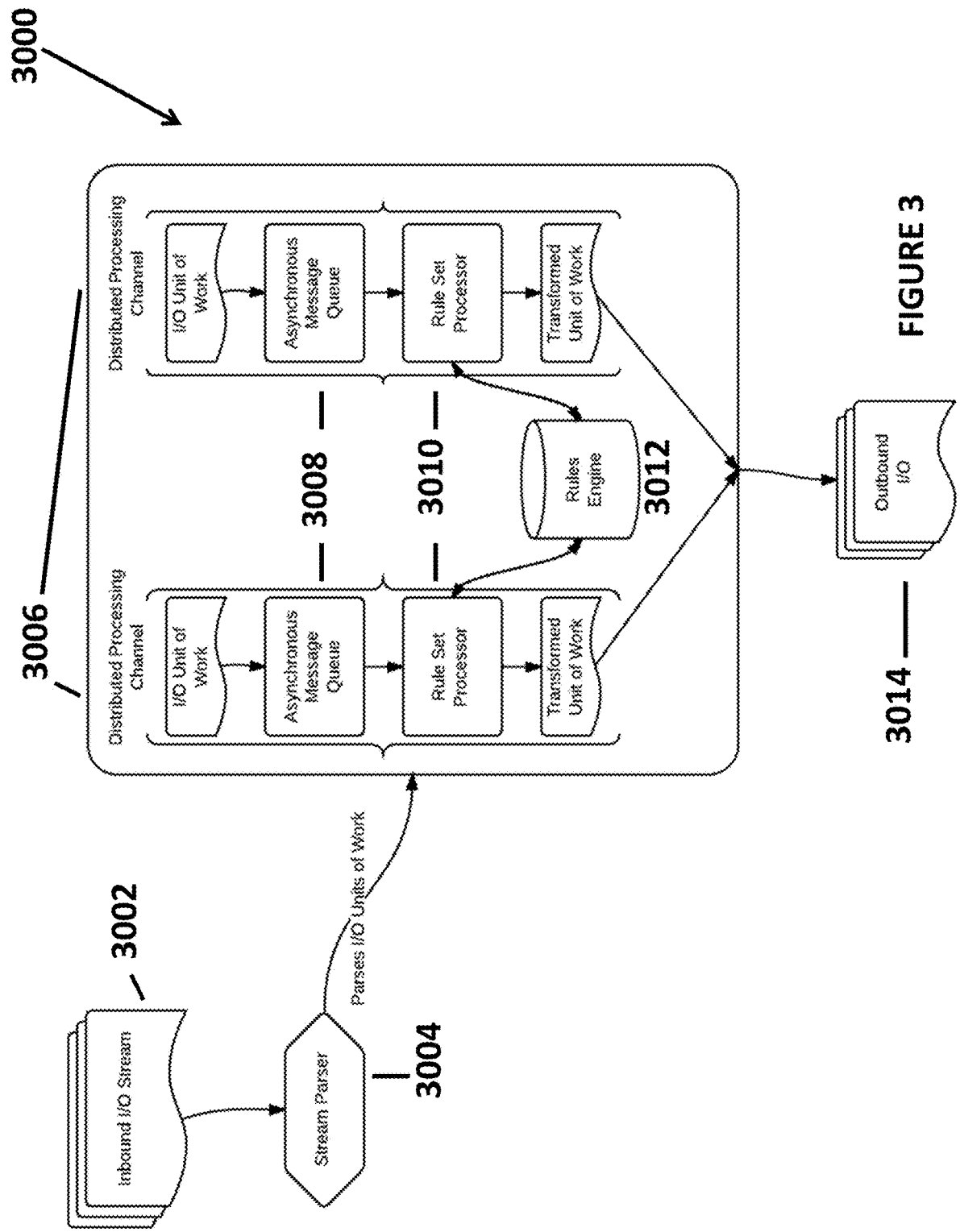
FIG. 3 illustrates the distributed and asynchronous process infrastructure used by the dynamic transactional data stream introspection and processing system of FIG. 1B.
Figure 4:
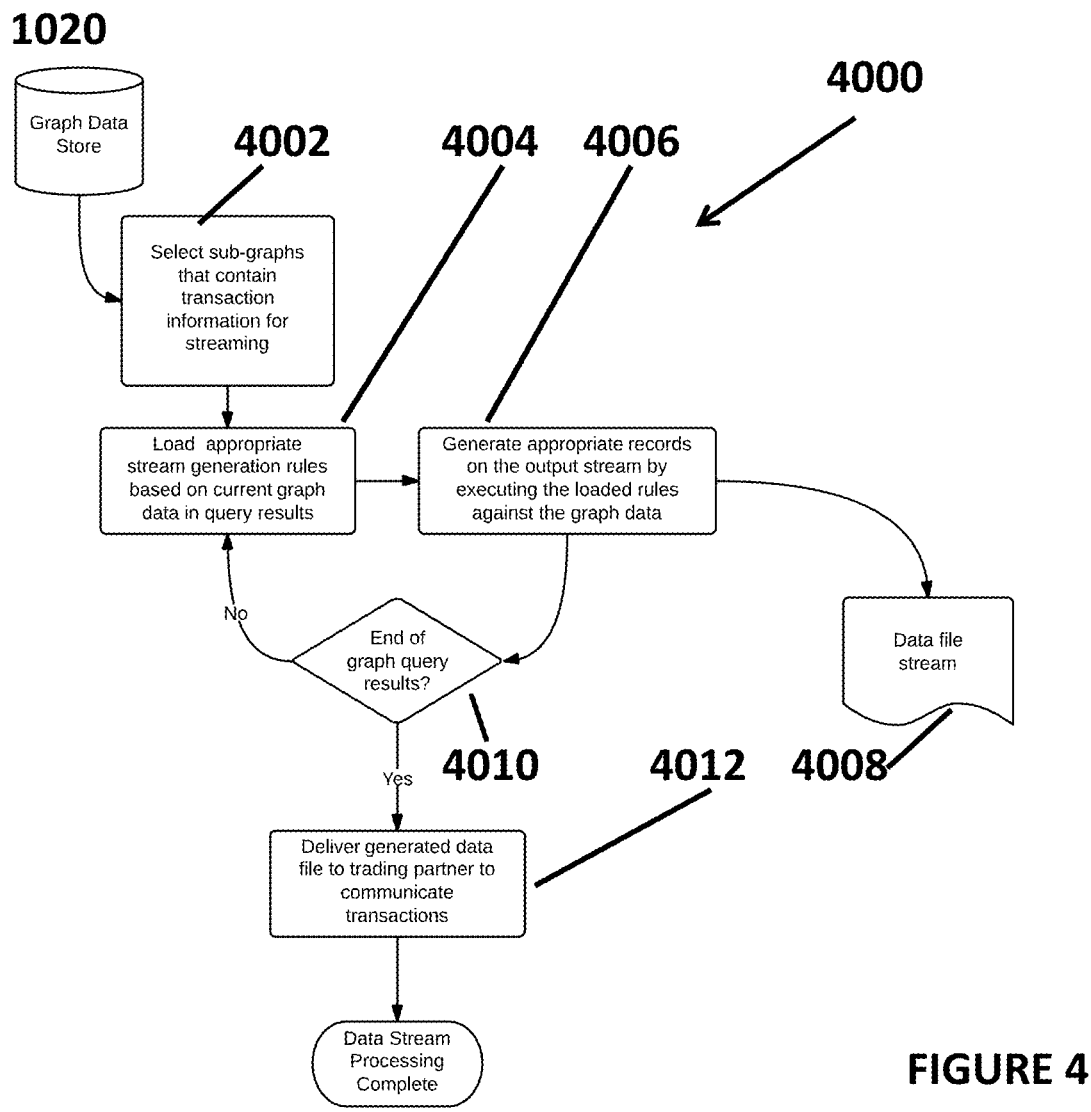
FIG. 4 illustrates an outbound transactional data stream processing method that may be implemented, for example, by the system shown in FIG. 5.
Figure 14:
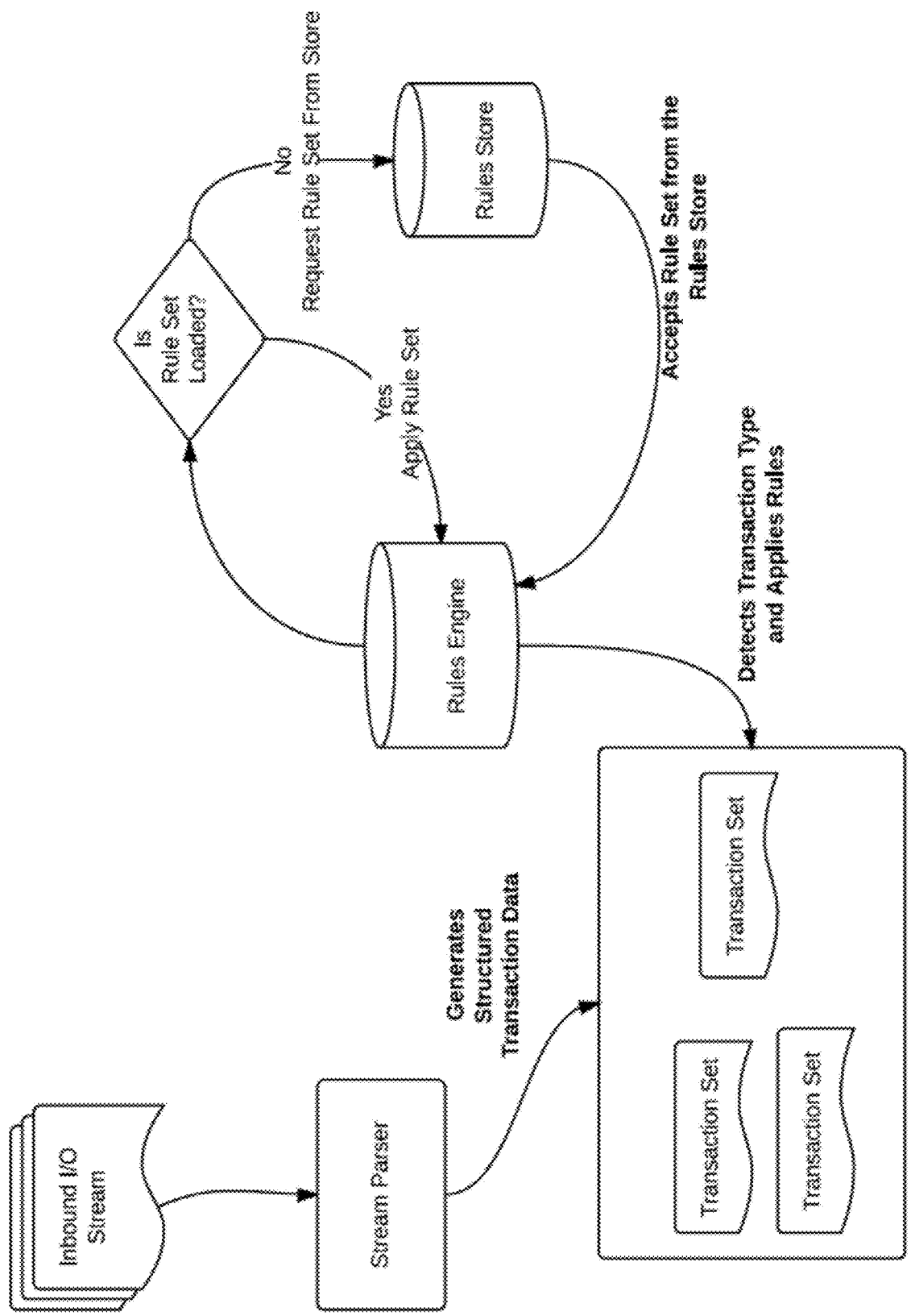
FIG. 14 illustrates how rule sets are dynamically loaded and applied to transaction sets.

FIG. 14 illustrates the how the system dynamically applies rules to transaction sets. A data stream containing multiple transaction sets, enters the system and is processed by a stream parser. The stream parser parses the input stream into the data into a structured format such as JSON. The transaction sets from the input stream are preserved in the structured format. The rules engine inspects each transaction set in the input stream, and determines which rule sets to apply, based on transaction set identifiers. Thus if an input stream contains multiple transaction sets, the rules engine is capable of dynamically loading the rule set on demand to process the transaction. Once the transaction set has been identified, the rules engine determines if the rule set is loaded. If the rule set is not loaded, the rules engine loads the rule set from the rule store. Finally, the rule set is applied to the transaction set. The rule set processing channels are illustrated in FIG. 3. The system 1500 may further comprise a data stream output component 1500D (details of the process is shown in FIG. 4) that generates an output data stream.

FIG. 2 illustrates the dynamic transactional data stream introspection and processing method (2000) utilized by the dynamic transactional data stream introspection and processing system 1500 of FIG. 1B. For example, the dynamic transactional data stream introspection and processing method (2000) may be implemented in the adapter component (1004) in the processing pipeline in FIG. 1A. The system may also receive input parameters identifying the input data source and it's transmission properties, such as the EDI sender, receiver, and payor identifiers, as well as data element separators. Transmission properties define the channel for the EDI transmission, specifying the transmission source and endpoint. As shown in FIG. 1A, the dynamic transactional data stream may have the adapter and connector components that the system inspects its input parameters and dynamically instantiates the adapter and connector components to handle the inbound request. The adapter forms requests and parse responses in a manner compatible with the channel's endpoint destination. The adapter also may transmit requests and receives responses via the connector component. The connector components provide data transmission services using protocols such as FTP, HTTP, SOAP. The process depicted in FIG. 2 activates rule sets based on the current transaction stream. The rule sets are used to read and parse data into a data structure which is then returned back to the caller.

FIG. 3 illustrates the processing environment used by the dynamic transactional data stream introspection and processing system shown in FIG. 1B. The processing environment is distributed across multiple processing channels. Processing operations are non-blocking due to the use of asynchronous messaging. Parallel processing is achieved through the use of multiple processing channels, where separate channels could refer to physically separate processing nodes, separate threads of execution, or a hybrid model where processing occurs on multiple nodes with each node using a multi-threaded environment. The inbound i/o stream (3002) is segmented into units of work by a stream parser (3004). The unit of work is specific to each transaction set, such as eligibility (270), enrollment (834), etc. Within each transaction set, the units of work are composed of segments which are composed of fields. The transaction set specific rule set is used to parse the unit of work from a transaction set.

The stream parser determines the appropriate unit of work by interrogating the inbound i/o stream, and then forwards the unit onto a processing channel (3006). A processing channel provides the services and execution environment for transforming the unit of work to the appropriate format. Within the processing channel, asynchronous message queues (3008) are used to support parallel processing within the distribution channel. Finally, a rule set processor (3010) is used to retrieve the appropriate rules from the system's rule engine (3012), and then apply these rules as described below to the unit of work as is described in more detail below in FIG. 3. Transformed units of work are coalesced into an outbound i/o stream (3014), which is then returned to the calling process.

Figure 5:
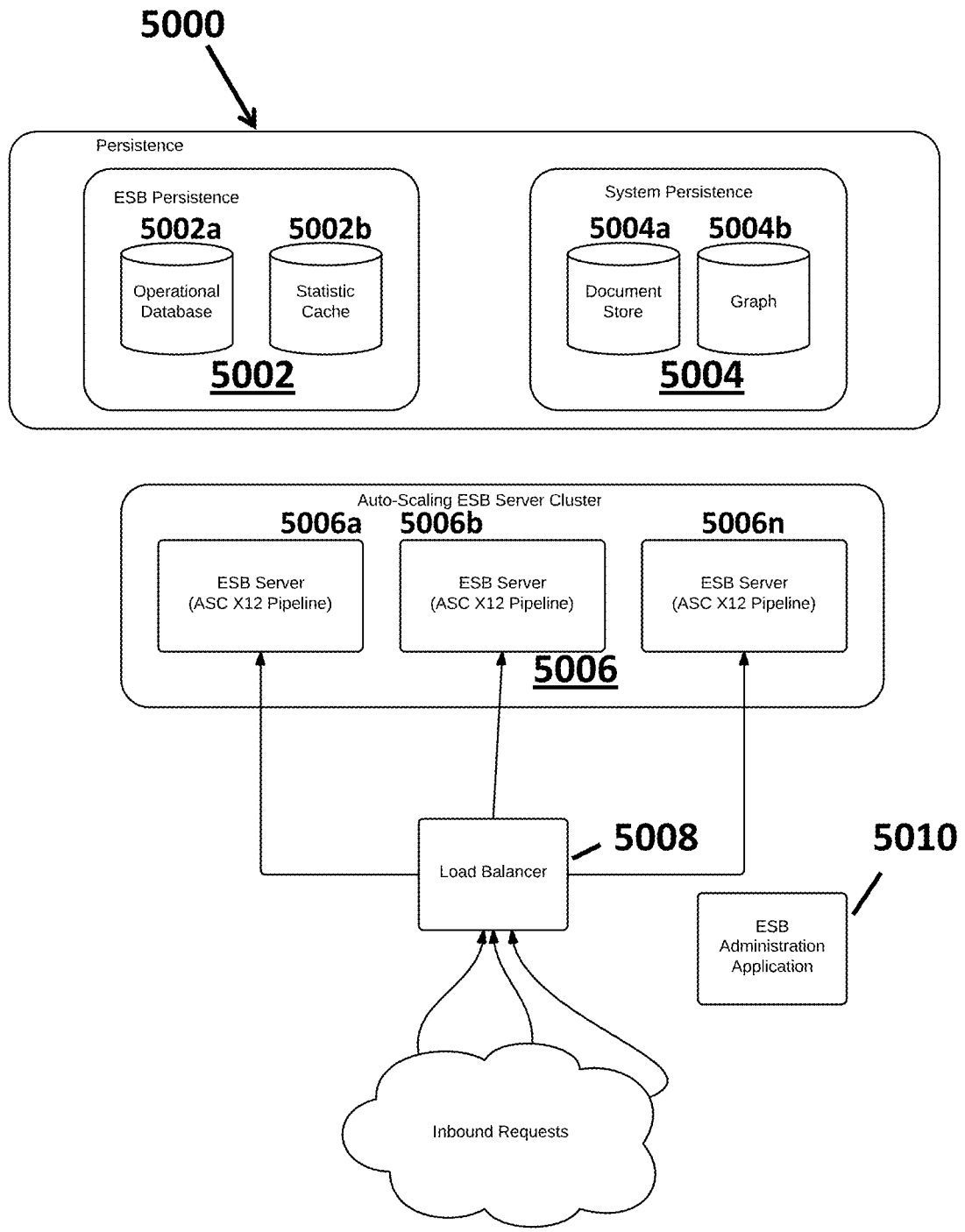
FIG. 5 illustrates an example of an implementation of dynamic data transactional system.
Figure 6:
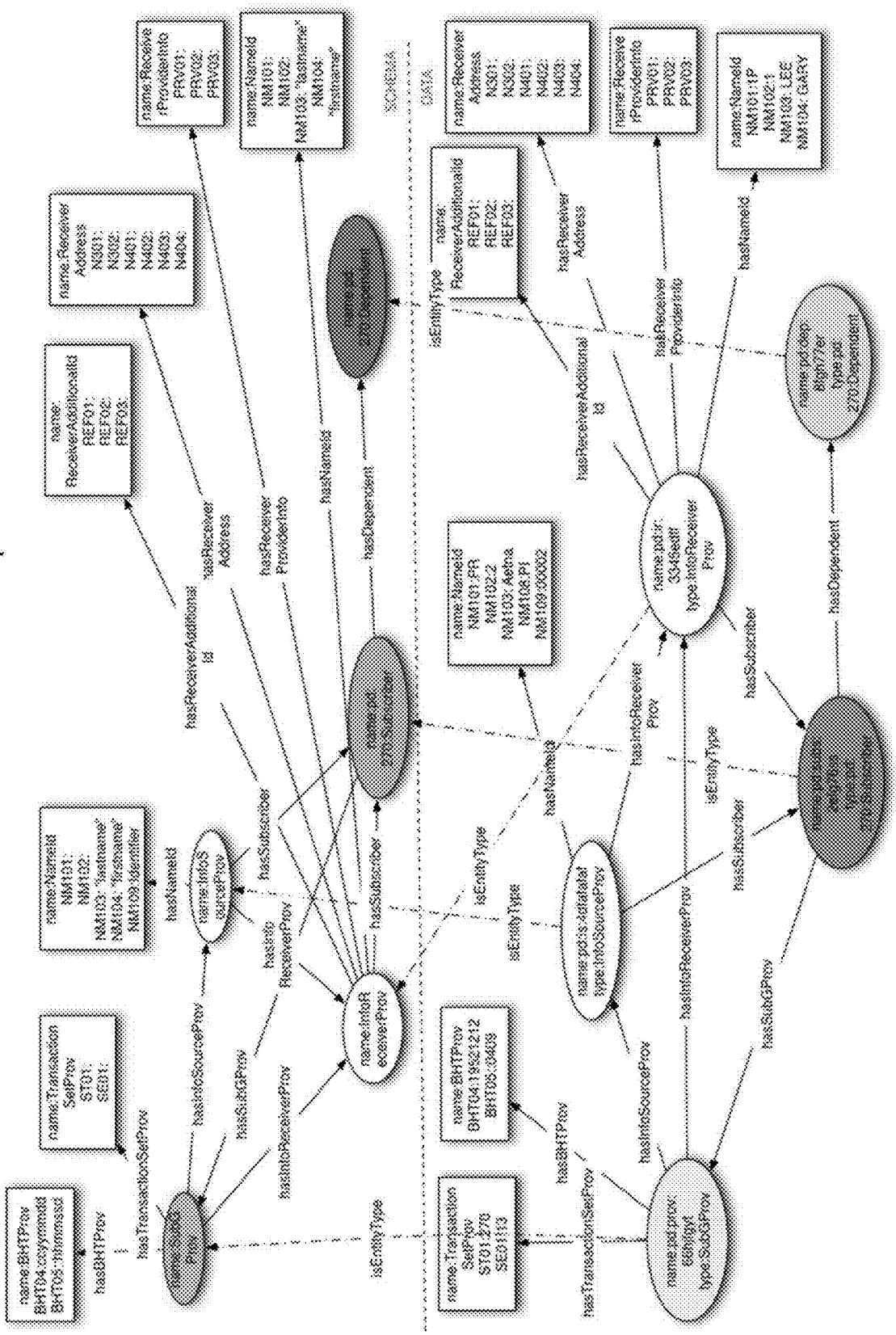
FIG. 6 illustrates an example of a 270 Provenance Graph that may be part of the system in FIGS. 1B and 5.
Figure 7:
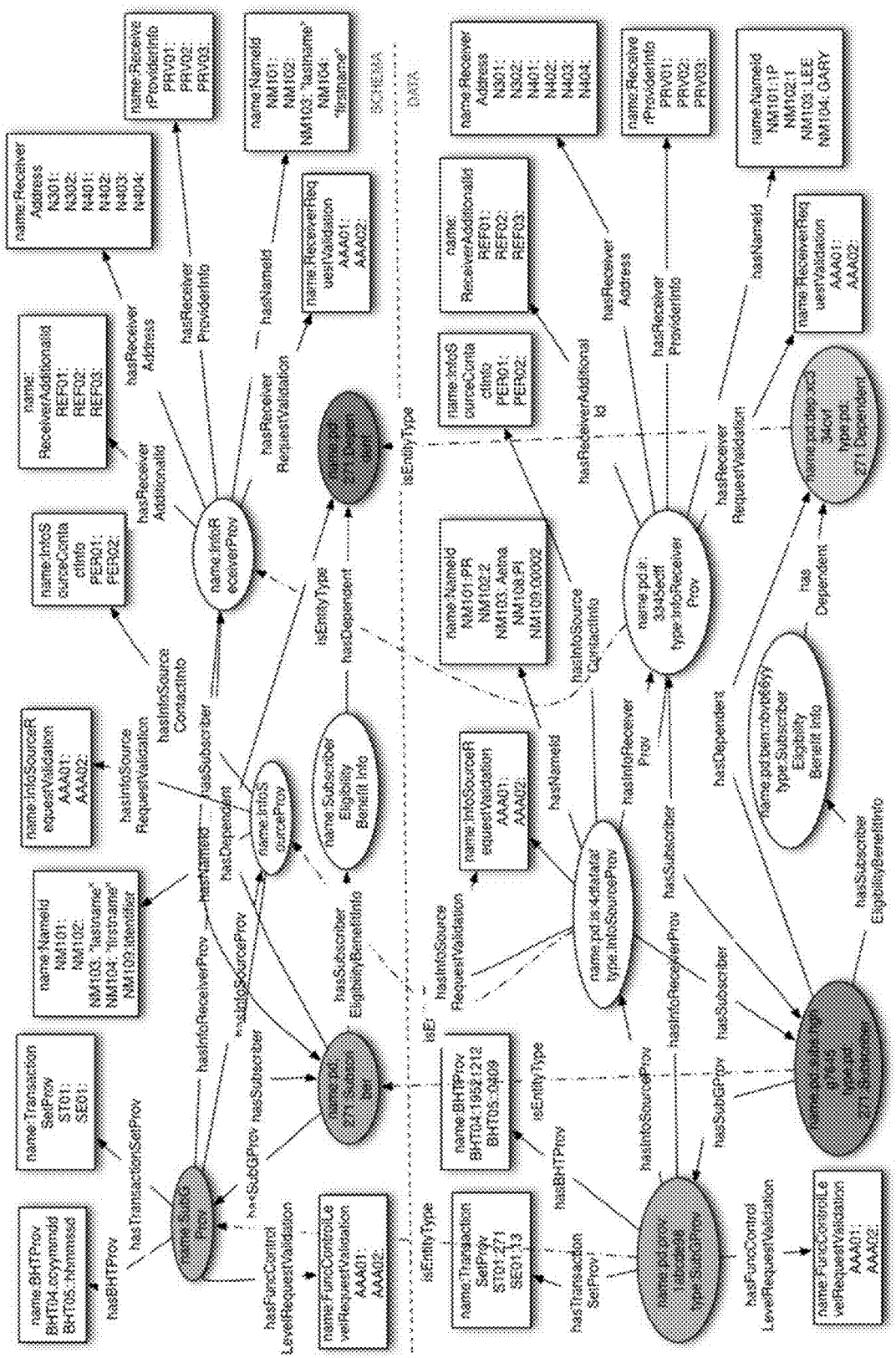
FIG. 7 illustrates an example of a 271 Provenance Graph that may be part of the system in FIGS. 1B and 5.
Figure 8:
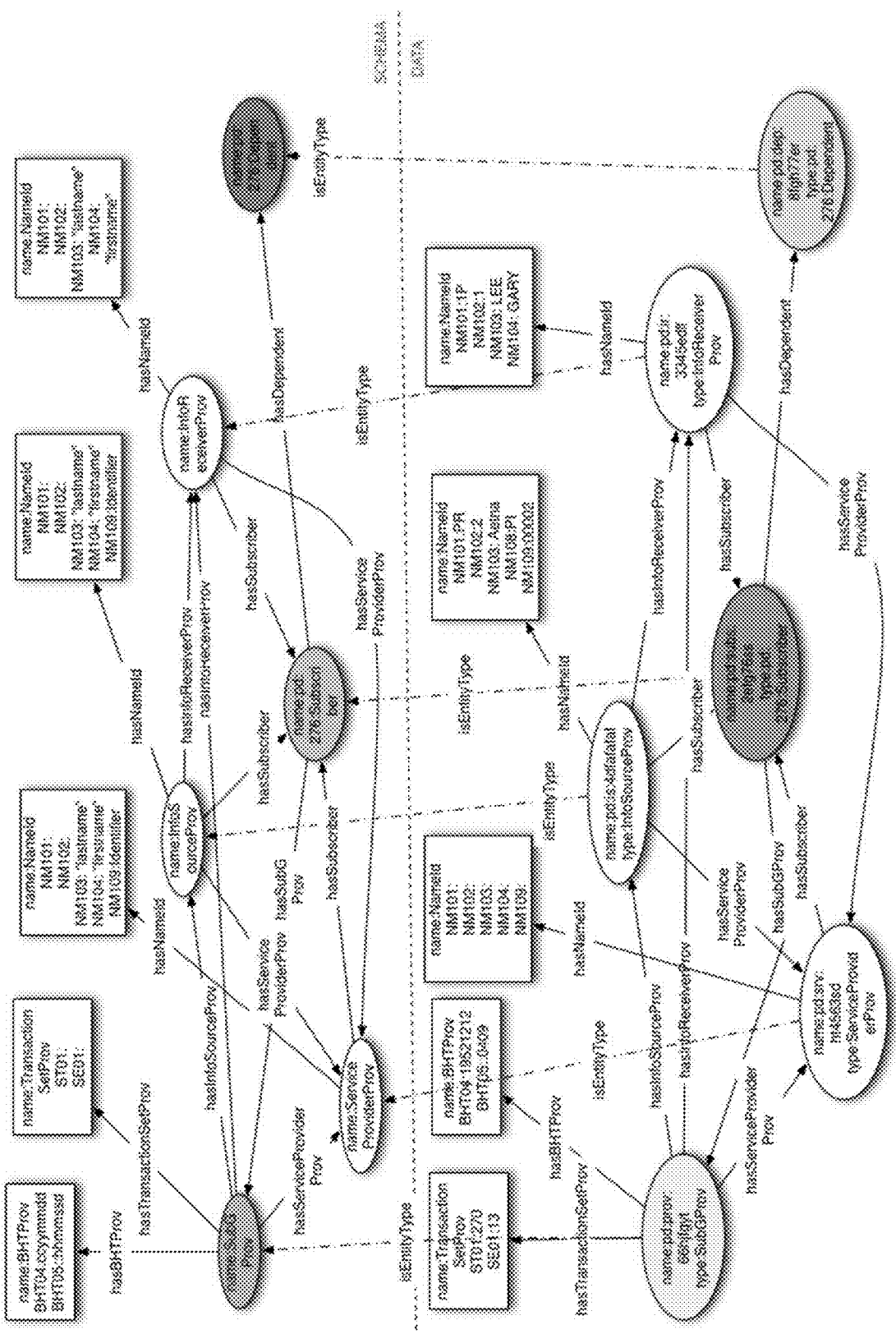
FIG. 8 illustrates an example of a 276 Provenance Graph that may be part of the system in FIGS. 1B and 5.
Figure 9:
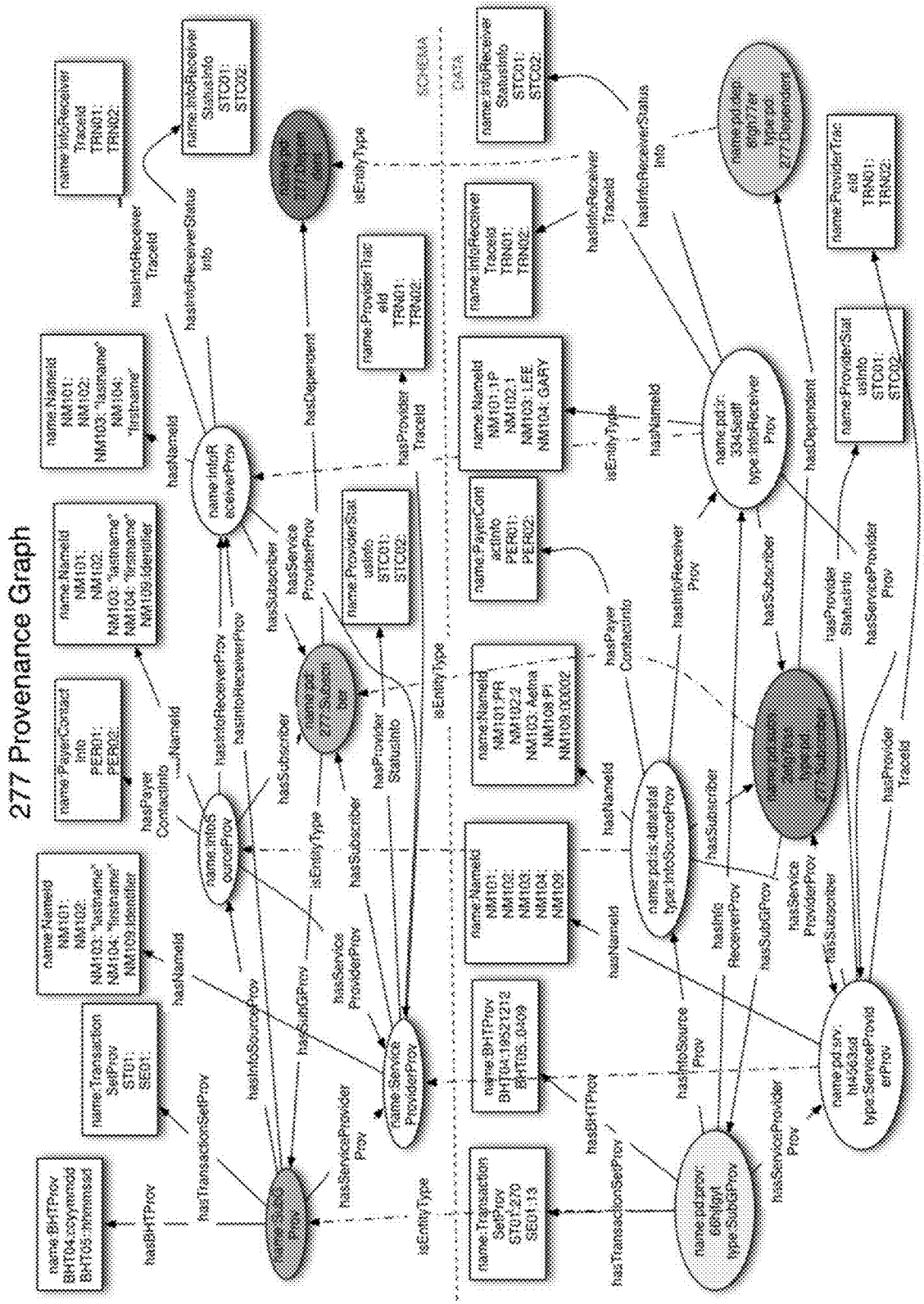
FIG. 9 illustrates an example of a 277 Provenance Graph that may be part of the system in FIGS. 1B and 5.

Referring back to FIG. 2, in the method, the system shown in FIG. 1B or 5 may inspect an incoming stream for the segments and type of data contained within the payload and may also receive a transaction data stream 2002 and the system may examine the transaction data to determine the element separator and segment terminator (2004.) The known ASC X12 5010 standard (more details of which may be found at http://www.cms.gov/Regulations-and-Guidance/HIPAA-Administrative-Simplification/Versions5010andD0/Version_5010.html, which is incorporated herein by reference) conveys data using a delimited format. In this format, data elements are separated using an element delimiter. Data elements are grouped into a larger structure referred to as a segment. Segments are delimited from one another using a segment terminator. The control characters used as the element separator and segment terminator are machine readable, and embedded within the ASC X12 5010 data stream. The system also may inspect the respective stream to determine which components are used to process the payload and components are associated with data elements by configuration in a configuration data store. Thus, the detection of the delimiters identifies each segment of the transactional datastream.

The system may activate an appropriate rule set based on the transaction set information (2006.) An example of the rules set based on transaction set information is discussed below with reference to the health care marketplace system scenario that shows how a healthcare marketplace system might use dynamic transactional data streaming during a consumer/health care provider interaction. The system may then read a next element from the data stream using the termination identifiers (2008.) The system may look up parse expression(s) for the data (2010) and parse the data based on the parse expression (2102.) An example of the parsing process is described below in the health care marketplace system scenario. The system may then apply rules to the parsed data (2014.) An example of this rule application process is described below in the health care marketplace system scenario.

The system may then determine if an end of the transaction set has been reached (2016) and loops back to 2008 to read the next segment if the end of the transaction set has not been reached. If the end of the transaction set has been reached, then the system may store the data generated by the rules into a graph form (2018) that may be stored in a graph data store 2020. For example, a graph model may be built with respect to the types of data that can be inferred across concerning the streams. Once the data is stored in a graph form, the system determines if more transaction sets need to be processed (2022) and the transaction data stream processing is completed if there are not any more transaction sets to be processed. If there are more transaction sets to be processed, then the system loops back to process 2006 to activate the appropriate rule set.

To better understand how this might work in practice; consider a scenario where a consumer and a health care provider are interacting within a health care marketplace system that utilizes this dynamic transactional data streaming technique. When the consumer first engages with the health care provider about a condition, the provider can utilize the health care marketplace system's eligibility check functionality to verify the consumer's health insurance and access their deductible information. The eligibility check functionality transmits a X12 270 transaction set (defined by the ASC X12 5010 standard above) to the consumer's insurance company to inquire about their deductible and general coverage information. When the insurance company responds with a X12 271 transaction set (defined by the ASC X12 5010 standard above) for benefit eligibility information, the system will use parse expressions based on the X12 file specifications defined by the ASC X12 5010 standard above in order to decompose segments in the transaction set into data elements. The parsed segment data is passed through a rules engine that is initialized with rules from a rule set that has been defined for the specific transaction set and trading partner. The following table includes some example parse expressions that would be used to parse segments found in a X12 271 transaction set:

| Example Parse Expressions for segments | Example Eligibility Inquiry Data Segments |
| --- | --- |
| HL*{HL01}*{HL02}*{HL03}*{HL04}~ | HL*3*2*22*0~ |
| NM1*{NM101}*{NM102}*{NM103}*{NM104}* {NM105}*{NM106}*{NM107}*{NM108}*{NM109}* {NM110}*{NM111}*{NM112}~ | NM1*IL*1*SMITH*JOHN*B***MI*W199100000~ |
| EB*{EB01}*{EB02}*{EB03}*{EB04}*{EB05}* {EB06}*{EB07}*{EB08}*{EB09}*{EB10}*{EB11}* {EB12}*{EB13}*{EB14}~ | EB*C*IND*30***23*3000*****Y~ |

Segment element IDs are defined in brackets, { }, inside each parse expression and may be optionally mapped to more meaningful variable names such that they may be referenced in rules by the more friendly variable name instead of the element ID.

A sample rule subset that can process segments found in a benefit eligibility inquiry response (271) transaction set is included in the table below along with sample data segments that would cause the rule(s) to execute:

| Example Rules for an Eligibility Inquiry Rule Set | Example Eligibility Inquiry Data Segments |
| --- | --- |
| "Hierarchical level rule": if the current segment has an id of "HL", then store the HL segment information in working memory for later use | HL*3*2*22*0~ |
| "Subscriber identification rule": if the current segment has an id of "NM1" and the "hierarchical level code" (or HL03 element id) in the current "HL" segment is "22" and the "entity identifier code" (or NM101 element id) in the "NM1" segment is "IL", then store the "NM1" segment information on the X12 domain model | NM1*IL*1*SMITH*JOHN*B***MI*W199100000~ |
| "Eligibility deductible information rule": if the current segment has an id of "EB" and the "eligibility/benefit information" (or EB01 element id) in the segment has a value of "C" then store the deductible information found in the segment on the X12 domain model | EB*C*IND*30***23*3000*****Y~ |

After verifying the consumer's health insurance, the provider examines the patient and makes a diagnosis. Since the provider did a general eligibility inquiry (X12 270) to determine the consumer's current deductible information, the provider is now equipped to recommend a set of treatment options that the consumer can pay for with cash or insurance. With a diagnosis and treatment(s) identified, the provider can initiate a more specific eligibility inquiry (X12 270) with codes (typically CPT or ICD-10) for the treatments to determine if the recommended treatments are covered by the consumer's insurance plan. This allows the consumer to make informed decisions regarding the treatments and their costs while they're still meeting with their health care provider. Once a treatment is selected, the health care marketplace system will record the treatment purchase transaction and submit the necessary X12 837 claims to the insurance company if the consumer elects to (partially) pay with insurance. If there is a portion of the treatment cost remaining after processing the X12 835 health care claim payment response, the health care marketplace system can then bill the consumer via their credit card on file and deposit the funds in the provider's bank account along with the insurance payment that was delivered in the X12 835 claim payment transaction set. Each X12 transaction set received by the health care marketplace system can make use of the dynamic transactional data streaming outlined in FIG. 2. For example, when a X12 271 transaction set is received following the benefits eligibility inquiry for the consumer visiting the health care provider, the 271 transaction data is examined (2004). After this examination, the appropriate rule set for the X12 271 transaction set is loaded into a rules engine (2006). For each data segment present in the 271 transaction set, the system will stream the segments through a stream based parser that will determine the appropriate parse expression based on the current segment's identifier (2008 and 2010). The segment data will be parsed according to the matched parse expression (2012) and then the parsed segment data will be loaded into the working memory for the rules engine so that the rules may be applied to the segment data (2014). The process of streaming in segments from the 271 transaction set, parsing them, and applying rules continues until the end of the transaction set is reached (2016). The eligibility information is stored in a graph data store once the transaction set is processed (2018 and 2020). This process may also be repeated for additional transaction sets that may be received from the insurance company (2022). The graph data stored in 2020 is available to the consumer and health care provider as part of the health care marketplace system.

FIG. 4 illustrates an outbound transactional data stream processing method 4000 that may be implemented, for example, by the system shown in FIGS. 1B and 5. In the method, the system may select sub-graphs that contain transactional information for streaming (4002) from the graph data store 1020 described above with reference to FIG. 1A. The system may then load appropriate stream generation rules based on current graph data in query results (4004) and generate appropriate records on the output stream by executing the loaded rules against the graph data (4006) which is communicated as a data file stream 4008.

The table below illustrates how the system utilizes rules to generate a claim status request (276) output stream using the graph data store domain.

| Claim Status Request Sample Rules | 276 X12 Output Stream Segments |
|---|---|
| "New Patient Record Rule": When the rules engine encouters a patient data attribute on the X12 domain model, add a new HL segment to the output stream to indicate the start of a new patient record. | HL*4*3*22*0~ |
| "Patient Birth Date and Gender Rule": When the patient has a date of birth and gender on the X12 domain model, add a new DMG segment to the output stream | DMG*D8*19191029*M~ |
| "Patient Identification Rule": When the patient has a name and member id, generate a NM1 segment and add it to the output stream | NM1*QC*1*DOE*JOHN****MI*R11056841~ |

After the appropriate records are generated, the system may determine if the end of the graph query results has been reached (4010) and delivers the generated data file(s) to a trading partner(s) to communicate the transaction (4012) if the end of the graph query results has been reached. If the end of the graph query results has not been reached, then the system may loop to process 4004 to load the appropriate rules.

FIG. 5 illustrates an example of an implementation of a dynamic data transactional system 5000 that may implement the methods described above. The system may be implemented using one or more computing resources (for example, cloud computing component(s) or server computer(s) with typical elements like processors and memory) and one or more components (including the adapter and connector components and some of the components in FIG. 5) that may be partially implemented by a plurality of lines of computer code. In another implementation, each of the components in FIG. 4 (and the adapter and connector components) may be implemented in hardware or a hardware device, such as a programmable logic device, an ASIC and the like.

Inbound requests are routed to a load balancer that distributes the processing load between one or more Enterprise Service Bus, ESB, and components. Each ESB is a software platform that hosts the ASC X12 Processing Pipeline and makes it available to external clients. The ESB utilizes two data stores, an operational database and a statistics cache to support its operations. The operational database tracks the services and components which are supported by the ESB. The statistics cache records service metrics such as the number of times a service has been executed, or a service's average response time. Both databases may be used to provide insight into the current health of the overall system. The system uses document and graph databases as depicted in FIG. 1. The ESB environment is maintained using the ESB administration application. The administration application is an operations console used to add, configure, and remove services, view processing statistics, and schedule recurring tasks. Each of the stores and the cache may be implemented as a software database or a hardware database.

Using the system, a transactional data file is communicated/received by a trading partner participating in data exchange. Trading Partner named herein, any other person or entity who will be receiving EDI information from or providing EDI information to another entity and who requires a submitter number because of a business need. Such person or entity may be an individual provider, a clinic composed of multiple providers, a clearinghouse or a billing agent. In the system, the graph model described above allows the X12 system that is historically row/column key-value based to be queried in a more knowledge domain model behavior. Furthermore, the system dynamically generates inter-domain relationships for nodes within the graph model. These graph relationships provide a holistic view of a member's data within a single system. In addition, the system may use Dynamic query based models that do not need traditional relational algebras.

Figure 10:
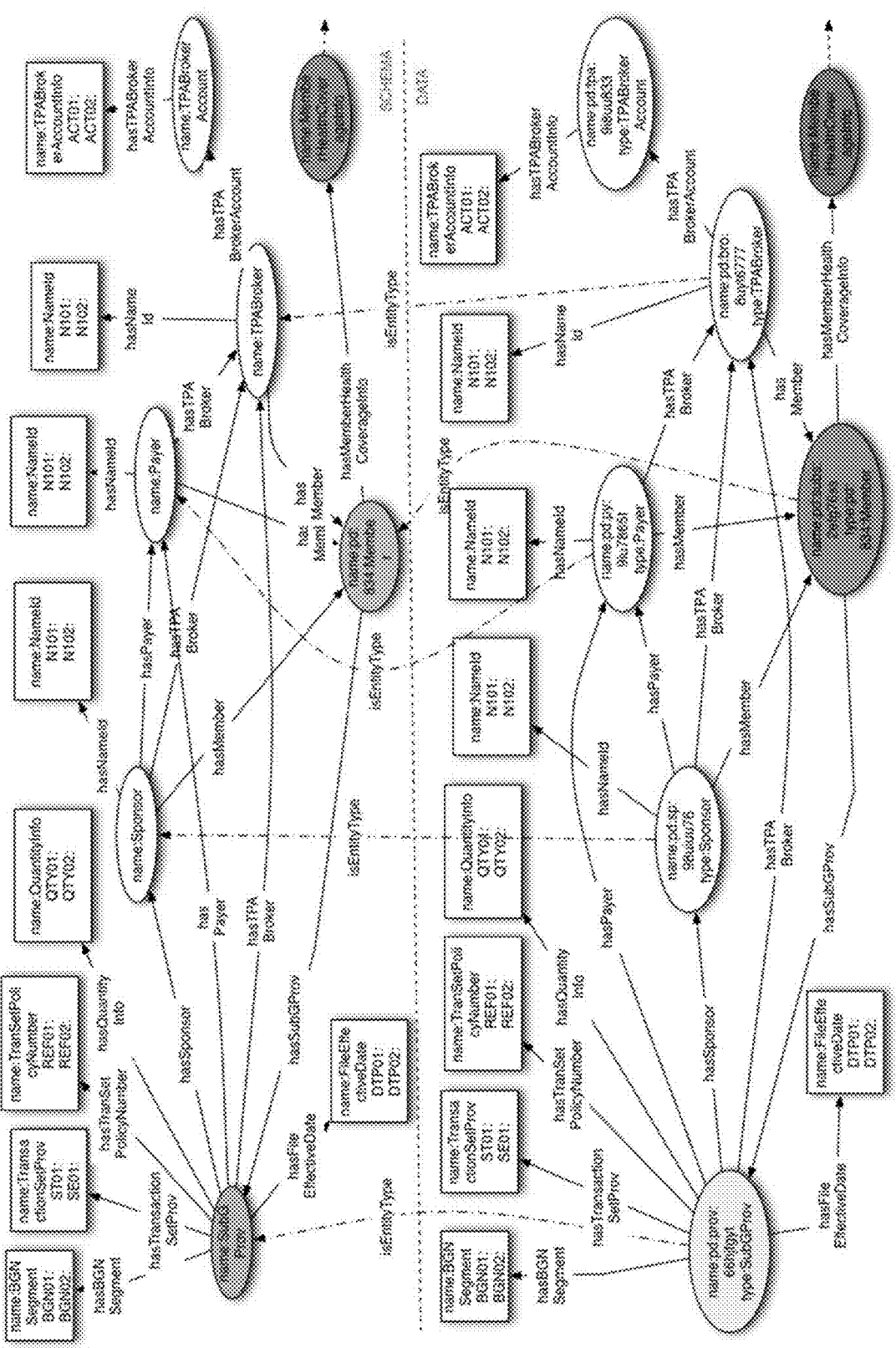
FIG. 10 illustrates an example of a 834 Provenance Graph that may be part of the system in FIGS. 1B and 5.
Figure 11:
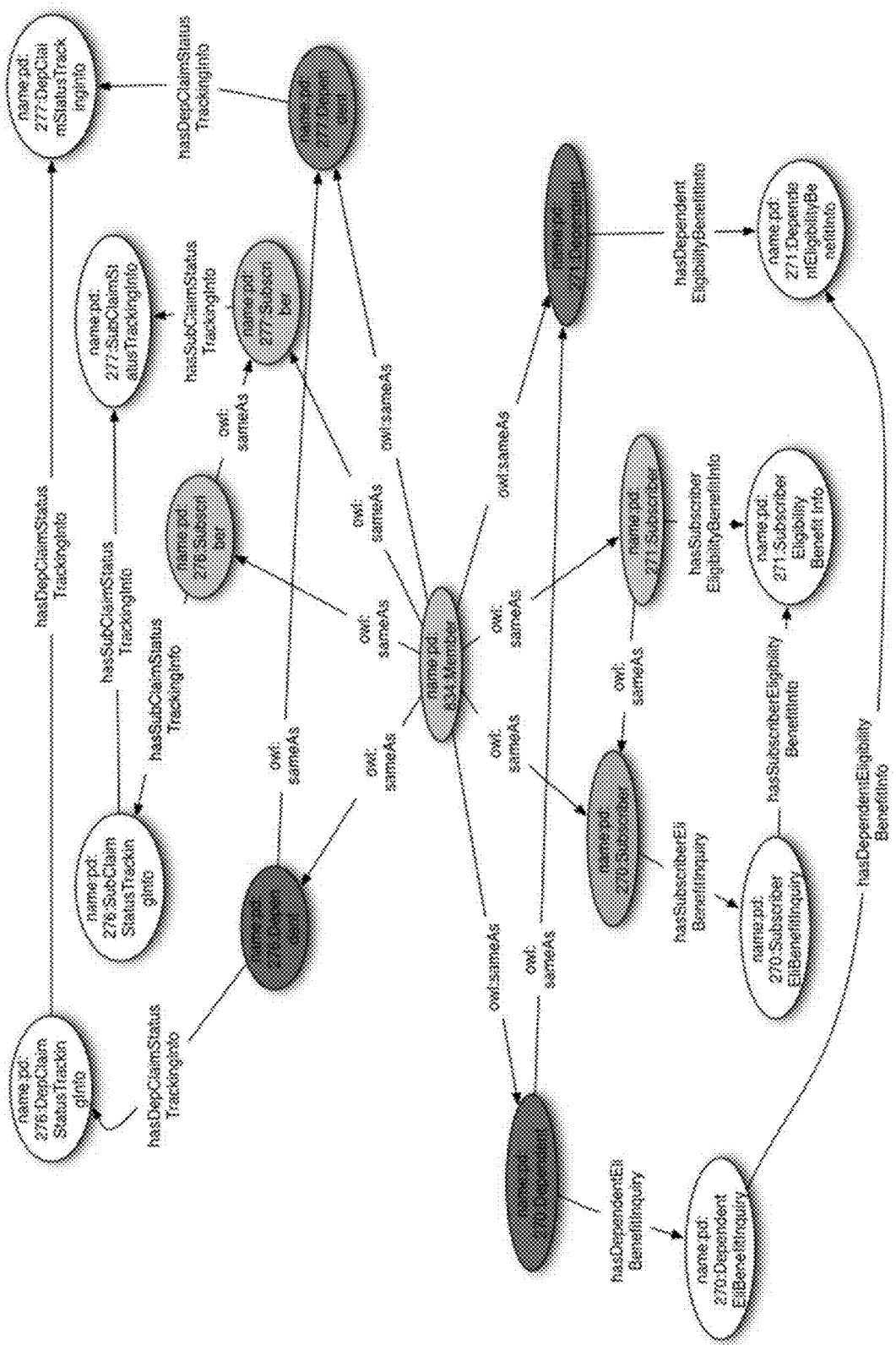
FIG. 11 illustrates an example of a ASCX12 5010 Inter-Domain Graph that may be part of the system in FIGS. 1B and 5.

FIGS. 6-10 illustrate the system's graph representation of ASC X12 5010 data segments. The transaction sets represented included: 270 (FIG. 6), 271 (FIG. 7), 276 (FIG. 8), 277 (FIG. 9), and 834 (FIG. 10). Each transaction set's graph representation includes schema and data nodes. Schema nodes are used to map ASC X12 5010 segment fields to domain names. The following example, from FIG. 6 maps "name" fields from the ASC X12 5010 name segment.

| Field Name | Domain Name |
|---|---|
| NM101 | Entity Identifier Code |
| NM102 | Entity Type Qualifier |
| NM103 | lastname |
| NM104 | firstname |

Data nodes store instances of persisted ASC X12 5010 data segments.

| Field Name | Data Value |
| --- | --- |
| NM101 | P |
| NM102 | 1 |
| NM103 | LEE |
| NM104 | GARY |

The graph system models the relationships between nodes. This information is used to associate node segments with one another using well defined relationships such as "hasDependent", "hasReceiverAddress", and "isEntity-Type". The system also establishes provenance, or origin, relationships which are used to associate nodes with parent or container nodes. These relationships preserve the ASC X12 5010 control envelopes used to convey transaction sets.

An example of a cypher graph queries that could be used to access graph data for outbound transactional data streaming may be:

```
start subGPProv = node:SubGProv(type= SubGProv) match tranSetProv<-
[:hasTransactionSetProv]-subGPProv-[:hasSubGProv]-member,member-
[:hasMemberNameInfo]-memberNameInfo-[:hasMemberName]-
memberName,member-[:hasMemberEmployerInfo]-
>memberEmployerInfo,memberEmployerName<-[:hasMemEmployerName]-
memberEmployerInfo-[:hasMemEmpCommunicationNumber]-
>memberEmpCommunicationNumber ,memberEmployerInfo-
[:hasMemEmpStreetAddress]->memberEmpStreetAddress where tranSetProv.ST01 =
834 and memberName.NM109 = 123456789 return
memberEmpCommunicationNumber,memberEmpStreetAddress,memberEmployerNa
me;
start subGPProv = node:SubGProv(type= SubGProv) match tranSetProv<-
[:hasTransactionSetProv]-subGPProv<-[:hasSubGProv]-member-
[:hasMemberNameInfo]->memberNameInfo-[:hasMemberName]-
>memberName,member-[:hasMemberHealthCoverageInfo]-
>memberHealthCoverageInfo-[:hasHealthCoverage]->healthCoverage where
tranSetProv.ST01 = 834 and memberName.NM109 = 123456789 return
healthCoverage;
```

A healthcare marketplace system may provide a transparent health services marketplace with clear descriptions and posted prices. Many health care providers and payers use legacy systems to communicate information for a variety of transactions: eligibility checks, claims processing and benefits enrollment. To integrate the healthcare marketplace system capabilities with existing systems in the health care space, it's important that it be able to process massive streams of transactional data related to health care services. The ability to process these transaction streams enables: real-time eligibility checks for quote requests, submitting a claim for a service after paying cash so that the service cost can contribute toward a deductible, enrolling a consumer in new health benefits so that they might save money on expensive services. Integrating all of these transaction capabilities with the health service marketplace provides consumers with easy access to information to help them make informed decisions concerning their health care spending. It also provides health care providers and payers with more efficiencies so that administrative costs for processing health care transactions approach zero. Without the dynamic transactional data streaming capabilities, consumers would only be able to use the healthcare marketplace system for cash based transactions and would have to consult other systems for insurance based pricing. The dynamic transactional data streaming may provide the best possible user experience for health care consumers and providers participating in the health care services marketplace.

Figure 12:
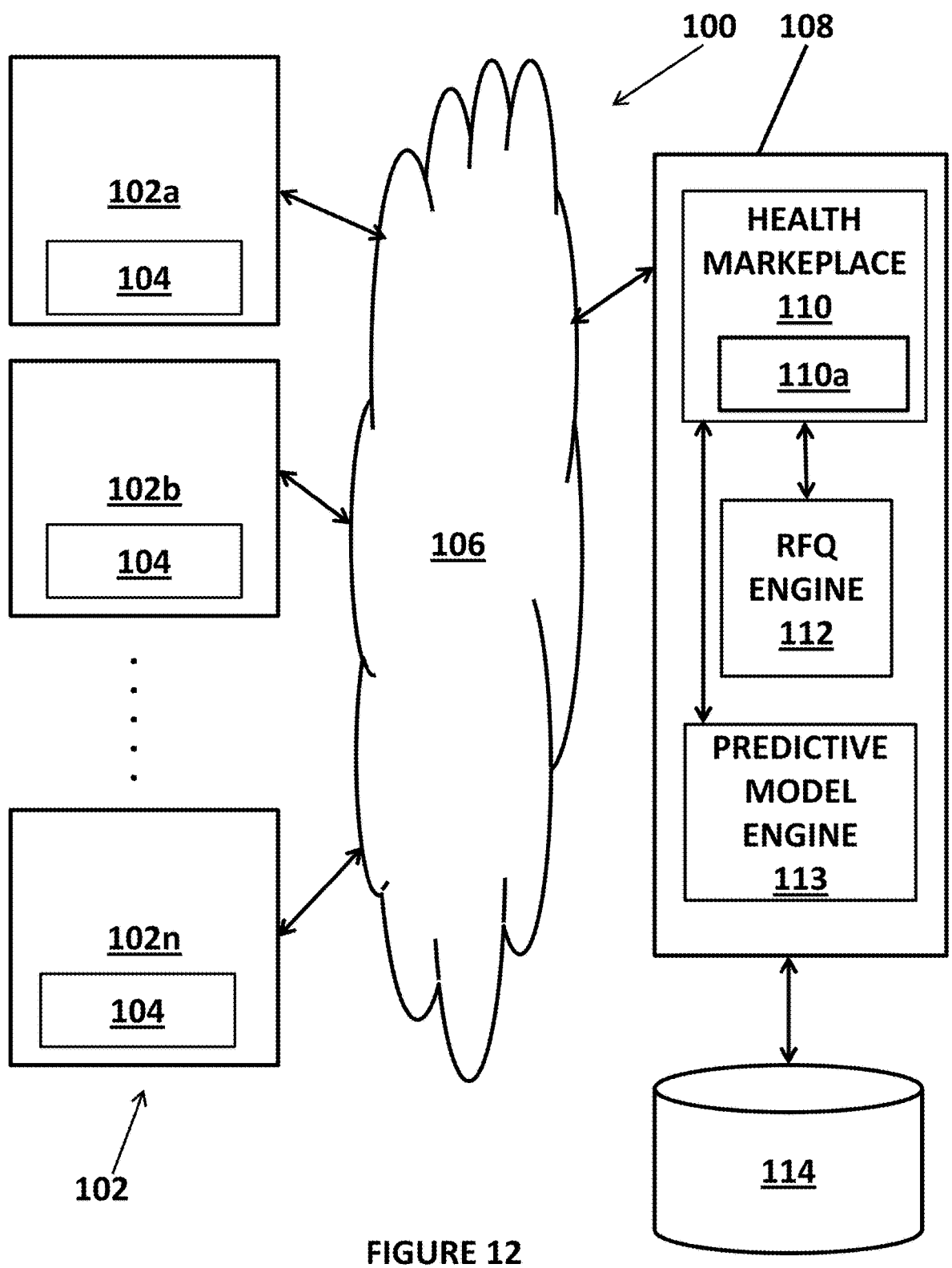
FIG. 12 illustrates an example of an implementation of a healthcare services marketplace system that may utilize the dynamic transaction system and method.

FIG. 12 illustrates an example of an implementation of a healthcare services marketplace system 100 that may utilize the dynamic transaction system and method. The healthcare marketplace system 100 may have one or more computing devices 102 that connect over a communication path 106 to a backend system 108. Each computing device 102, such as computing devices 102a, 102b, . . . , 102n as shown in FIG. 12, may be a processor based device with memory, persistent storage, wired or wireless communication circuits and a display that allows each computing device to connect to and couple over the communication path 106 to a backend system 108. For example, each computing device may be a smartphone device, such as an Apple Computer product, Android OS based product, etc., a tablet computer, a personal computer, a terminal device, a laptop computer and the like. In one embodiment shown in FIG. 12, each computing device 102 may store an application 104 in memory and then execute that application using the processor of the computing device to interface with the backend system. For example, the application may be a typical browser application or may be a mobile application. The communication path 106 may be a wired or wireless communication path that uses a secure protocol or an unsecure protocol. For example, the communication path 106 may be the Internet, Ethernet, a wireless data network, a cellular digital data network, a WiFi network and the like.

The backend system 108 may also have a health marketplace engine 110, a request for quote engine 112 and a predictive pricing engine 113 that may be coupled together. Each of these components of the backend system may be implemented using one or more computing resources, such as one or more server computers, one or more cloud computing resources and the like. In one embodiment, the health marketplace engine 110, the request for quote engine 112 and the predictive modeling engine 113 may each be implemented in software in which each has a plurality of lines of computer code that are executed by a processor of the one or more computing resources of the backend system. In other embodiments, each of the health marketplace engine 110, the request for quote engine 112 and the predictive modeling engine 113 may be implemented in hardware such as a programmed logic device, a programmed processor or microcontroller and the like. The backend system 108 may be coupled to a store 114 that stores the various data and software modules that make up the healthcare system. The store 114 may be implemented as a hardware database system, a software database system or any other storage system. In this example implementation, the dynamic transaction system components described above may be incorporated into the backend system 108 or may be coupled to the backend system 108, but located remotely.

The health marketplace engine 110 may allow practitioners that have joined the healthcare social community to reach potential clients in ways unimaginable even a few years ago. In addition to giving practitioners a social portal with which to communicate and market themselves with consumers, the marketplace gives each healthcare practitioner the ability to offer their services in an environment that is familiar to users of Groupon, Living Social, or other social marketplaces.

The request for quote engine 112, in the example shown in FIG. 12 in which the request for quote engine 112 is part of the health marketplace system 110, allows a user of the health marketplace system to search for practitioners in their area that treat their conditions or practice in a desired specialty and request a quote for the service they need. Further details of the request for quote engine 112 are provided in U.S. Patent Application Ser. No. 61/871,195, filed on Aug. 28, 2013 and U.S. patent application Ser. No. 14/328,591 filed on Jul. 10, 2014, the entirety of both of which are incorporated herein by reference. The predictive modeling engine 113 may generate healthcare service prices based on predictive modeling. Further details of the predictive modeling engine 113 are provided in U.S. Patent Application Ser. No. 61/881,918, filed on Sep. 24, 2013 and U.S. patent application Ser. No. 14/455,341 filed on Aug. 8, 2014, the entirety of both of which are incorporated herein by reference.

The health marketplace system 110 may further have a health management engine 110*a* that may generate a healthstream for each member who is a user of the health system 100 and who has logged into the health system 100. The healthstream groups health related information and events into a timeline that can be shared among a patient, healthcare provider(s), and approved family members/friends of each member/user of the system. The information for each user/member may be entered directly into the healthstream using the application 104. Alternatively or in addition, the information about the user/member may also be imported from entries made in other systems including Facebook, Twitter, Foursquare and other web sites. Although the keeping of a detailed health journal requires a lot of discipline and work and busy lives don't often have time to keep up with it, a lot of important health information about the user/member may be recorded all the time in social networks and web sites. The healthstream may provide users an easy way to import and organize information that has already been recorded in these other systems so that it can be visualized as a timeline of health information.

The health timeline (that is part of the healthstream) may always be available for review by approved members of the PokitDok community (healthcare providers, family members, friends) who have the required access rights and privileges that may be set up by the user. The system may allow a user/member to link an account in the health system, such as the health system provided by PokitDok, with other accounts that have been established by the user/member using a known OAuth authorization flow (further details of which may be found at http://en.wikipedia.org/wiki/OAuth which is incorporated herein by reference.) The OAuth flow links the accounts of the user (social network and web accounts) so that the system is able to gather health related information. Once the accounts are linked, the application 104 on the computing device may make API calls to each linked system to import health related posts into their healthstream. In addition, users may be able to drag and drop entries to and from their healthstream to quickly manage what's permanently stored there.

In the health system, the timeline view generated for each user/member may support multiple cases in the timeline view. Each case may be like a directory on a filesystem where events may be stored together. For example, a mother may have cases defined for herself and for her young children that are not yet old enough to manage their own healthstream. When that mother uses the PokitDok healthstream, her checkins at the doctor's office will be imported into her case folder. When she posts about her child running a fever on facebook, that event will be imported into her child's case folder that may be done by utilizing the APIs provided by the various social networks and systems that can be linked to a PokitDok account. Each time a PokitDok user returns to the system, asynchronous tasks are queued to process the latest data from their linked accounts. The results of the above tasks may be presented in a list in the application. Each entry in that list may be manually added to a case using the drag and drop capabilities of HTML5. In addition, when possible, imported entries may be automatically added to cases by analyzing the imported content for health related keywords.

The health system may support a variety of healthstream entry types. For example, when a checkin is added to the healthstream, a link to the location is stored along with geolocation information so it can be quickly displayed on a map view. As another example, when entries with photos are added to the healthstream, a link to the original photo is stored along with cached versions of the photo at various resolutions for display in different contexts. The healthstream may also include entries about medications that may be added to the timeline that include information about when a medication was started/stopped along with dosage details for the medication. In addition, doctor appointments may also be added to the healthstream. Furthermore, healthstream video entries contain links to the original video so that it may be embedded in the health timeline along with the other information. In addition to the specific healthstream entry types above, a generic entry type may be available that supports miscellaneous file attachments. For example, a user may have a PDF of blood results that were emailed to them that they want to add to their healthstream so that it can be shared with other health providers also on that case. The healthstream may allow a user to drag the PDF attachment from their email to the appropriate case in their timeline.

In the system 100, each of the entries for a user may be stored in the store 114 with a user's globally unique identifier and the identifiers of other PokitDok users that are allowed to view the information to provide, among other things, access control for the data in the healthstream of each user. In the system, each entry may default to being private among the users explicitly specified on the data. Users can choose to change the privacy level to 'anonymous' when they want to share information they've learned about a particular health issue with the community without revealing their identity.

Healthcare providers that are part of a healthstream case for a user can also add events to it. For example, a provider can review a user's healthstream when meeting with them and recommend a service they've posted on the health marketplace as part of their treatment plan. This may add that service to the healthstream with a date/time stamp so the patient and other healthcare providers are all up-to-date with currently active treatments and medications. If multiple providers are participating on a case, email and SMS alerts can be triggered to alert them that new information is available for their review.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A dynamic transactional data streaming system, comprising:
   a data streaming system;
   the data streaming system having a storage device that stores a plurality of rule sets, wherein each rule set processes a corresponding electronic healthcare transactional datastream each having a particular set of healthcare transactional data;
   the data streaming system having a data stream examination component configured to receive one of the corresponding electronic healthcare transactional datastreams in a first format, the received electronic healthcare transactional datastream having one or more transaction sets delimited by a first set of segments and one or more pieces of data elements within each transaction set delimited by a second set of segments, the data stream examination component also comprising a stream parser configured to identify each of the segments in the electronic healthcare transactional datastream and parse each of the segments into a unit of work having a structured format different from the first format, wherein the received electronic healthcare transactional datastream comprises a real-time healthcare insurance eligibility check for quote requests, a health claim for a health service after a consumer pays cash for at least a portion of a health claim so that a service cost for the health claim can contribute toward an insurance deductible, or enrolling the consumer in new health insurance benefits so that the consumer saves money on expensive health services; and
   the data streaming system having a data stream processing component, the data stream processing component comprising a plurality of distributed processing channels, each distributed processing channel having:
      an asynchronous message queue to communicate with each of the other distributed processing channels and support parallel processing in the plurality of distributed processing channels of each unit of work in the electronic healthcare transactional datastream,
      a rule set processor configured to select a rule set from the plurality of rule sets based on the data elements in each transaction set of the electronic healthcare transactional datastream, wherein each distributed processing channel generates a transformed unit of work based on the selected rule set and the unit of work and coalesces the transformed units of work from the plurality of distributed processing channels into a set of translated data that is translated from the structured format to the first format, based on the selected rule set and the plurality of segments and the plurality of data elements of the electronic healthcare transactional datastream; and
   wherein the data streaming system is configured to output a claim status request output stream using the set of translated data, and
   wherein the claim status request output stream comprises a response to the real-time healthcare insurance eligibility check for quote requests, a response to the submission of a health insurance claim for a health service after the consumer pays cash for at least the portion of the health claim so that the service cost for the health claim can contribute toward the insurance deductible, or a response to enrolling the consumer in new health insurance benefits so that the consumer saves money on expensive health services.

2. The system of claim 1, wherein the data stream segment processing component is configured to parse each data element in each segment based on a parse expression to generate a parsed data element and configured to apply the selected rule set to the parsed data element.

3. The system of claim 2, wherein the set of translated data is stored in a graph.

4. The system of claim 1, wherein the data stream examination component that is configured to identify each of the segments in the electronic healthcare transactional datastream is further configured to identify an element delimiter that separates each data element and a segment terminator that separates each segment in the electronic healthcare transactional datastream.

5. The system of claim 1 further comprising a data stream output component configured to load a stream generation rule based on the set of translated data and configured to generate an output datastream using the stream generation rule and the set of translated data.

6. The system of claim 5, wherein the data stream output component loads the stream generation rules based on a set of translated data stored in a graph.

7. The system of claim 1, wherein the electronic healthcare transactional datastream is a healthcare transactional datastream.

8. The system of claim 7, wherein the healthcare transactional datastream uses a health care delimited format having a set of health care related transactions and code sets.

9. The system of claim 1, wherein the data stream system further comprises a data processing component having a plurality of processing channels wherein each processing channel processes a segment of the transactional data so that the data segments of the transactional datastream are processed in parallel.

10. The system of claim 9, wherein each processing channel has a message queue so that each processing channel communicates with the other processing channels.

11. The system of claim 9, wherein each processing channel is a thread executed by a processor.

12. The system of claim 9, wherein each processing channel has a rule set processor that performs the operations of the data stream segment processing component for each segment assigned to the processing channel.

13. A dynamic transactional data streaming method, comprising:
   storing, in a storage device, a plurality of rule sets, wherein each rule set processes a corresponding electronic healthcare transactional datastream each having a particular set of transactional data;
   receiving, by a computer system coupled to the storage device, one of the corresponding electronic healthcare transactional datastreams in a first format, the received electronic healthcare transactional datastream having one or more transaction sets delimited by a first set of segments and one or more pieces of data elements within each transaction set delimited by a second set of segments;
   identifying, by a stream parser of the computer system, each of the segments in the electronic healthcare transactional datastream, and parsing each of the segments into a unit of work having a structured format different from the first format, wherein the received electronic healthcare transactional datastream comprises a real-time healthcare insurance eligibility check for quote requests, a health claim for a health service after a consumer pays cash for at least a portion of a health claim so that a service cost for the health claim can contribute toward an insurance deductible, or enrolling the consumer in new health insurance benefits so that the consumer saves money on expensive health services;

parallel processing, by a data stream processing component of the computer system, a plurality of distributed processing channels, each unit of work;

communicating, by an asynchronous message queue in each distributed processing channel, with each of the other distributed processing channels to support the parallel processing in the plurality of distributed processing channels of each unit of work in the electronic healthcare transactional datastream;

selecting, by the computer system, a rule set from the plurality of rule sets based on the data elements in each segment of the electronic healthcare transactional datastream;

generating, by each distributed processing channel, a transformed unit of work based on the selected rule set and the unit of work;

coalescing, by the computer system, the transformed units of work from the plurality of distributed processing channels into a set of translated data that is translated from the structured format to the first format, based on the selected rule set and the plurality of segments and the plurality of data elements of the electronic healthcare transactional datastream; and outputting a claim status request output stream using the set of translated data, wherein the claim status request output stream comprises a response to the real-time healthcare insurance eligibility check for quote requests, a response to the submission of a health insurance claim for a health service after the consumer pays cash for at least the portion of the health claim so that the service cost for the health claim can contribute toward the insurance deductible, or a response to enrolling the consumer in new health insurance benefits so that the consumer saves money on expensive health services.

14. The method of claim 13 further comprising parsing, by the computer system, each data element in each segment based on a parse expression to generate a parsed data element and applying, by the computer system, the selected rule set to the parsed data element.

15. The method of claim 14 further comprising storing the set of translated data in a graph.

16. The method of claim 13, wherein identifying each segment further comprises identifying, by the computer system, an element delimiter that separates each data element and a segment terminator that separates each segment in the electronic healthcare transactional datastream.

17. The method of claim 13 further comprising loading, by the computer system, a stream generation rule based on the set of translated data and generating, by the computer system, an output datastream using the stream generation rule and the set of translated data.

18. The method of claim 17, wherein loading the stream generation rules further comprising loading, by the computer system, the stream generation rule based on a set of translated data stored in graph.

19. The method of claim 13, wherein the electronic healthcare transactional datastream is a healthcare transactional datastream.

20. The method of claim 19, wherein the healthcare transactional datastream uses a health care delimited format having a set of health care related transactions and code sets.

* * * * *